(12) United States Patent
Marcelpoil et al.

(10) Patent No.: US 7,133,547 B2
(45) Date of Patent: Nov. 7, 2006

(54) METHOD FOR QUANTITATIVE VIDEO-MICROSCOPY AND ASSOCIATED SYSTEM AND COMPUTER SOFTWARE PROGRAM PRODUCT

(75) Inventors: Raphaël Marcelpoil, Grenoble (FR); Didier Morel, Grenoble (FR)

(73) Assignee: TriPath Imaging, Inc., Burlington, NC (US)

( * ) Notice: Subject to any disclaimer, the term of this patent is extended or adjusted under 35 U.S.C. 154(b) by 840 days.

(21) Appl. No.: 10/057,729

(22) Filed: Jan. 24, 2002

(65) Prior Publication Data
US 2003/0138140 A1 Jul. 24, 2003

(51) Int. Cl.
*G06K 9/00* (2006.01)
(52) U.S. Cl. .................. 382/129; 382/162; 356/39; 348/453
(58) Field of Classification Search .............. 382/129, 382/162, 128, 165, 131, 133; 128/922; 356/39; 436/66; 359/326; 348/453
See application file for complete search history.

(56) References Cited

U.S. PATENT DOCUMENTS

| | | | |
|---|---|---|---|
| 4,191,940 A | | 3/1980 | Polcyn et al. |
| 4,887,892 A | | 12/1989 | Bacus |
| 4,997,769 A | * | 3/1991 | Lundsgaard ............. 436/66 |
| 4,998,284 A | | 3/1991 | Bacus et al. |
| 5,008,185 A | | 4/1991 | Bacus |
| 5,025,061 A | * | 6/1991 | Ishidoya et al. ......... 524/539 |
| 5,109,429 A | | 4/1992 | Bacus et al. |
| 5,134,662 A | | 7/1992 | Bacus et al. |

(Continued)

FOREIGN PATENT DOCUMENTS

EP 1 065 496 A2 1/2001

(Continued)

OTHER PUBLICATIONS

Deeds, et al., "Patterns of Melastatin mRNA Expression in Melanocytic Tumors", Abstract, *Hum Pathol*, 2000, pp. 1346-1356, vol. 31(11).

(Continued)

*Primary Examiner*—Barry Choobin
(74) *Attorney, Agent, or Firm*—Alston & Bird LLP

(57) ABSTRACT

A method of determining an amount of at least one molecular species in a sample from an image of the sample captured by an image acquisition device is provided, each molecular species being indicated by a dye. A dye space representation of a plurality of dyes is formed by orthogonally adding the correspondence tables of the dyes, each correspondence table having a plurality of normalized RGB triplets and incrementally extending from 0% to 100% transmittance. The dye space representation has one dimension for each dye and provides a reference model for a combination of the plurality of dyes. Each pixel of an image of the sample stained with the combination of the plurality of dyes is compared to the reference model, each pixel having a color defined by an RGB triplet, so as to determine an optimal combination of normalized RGB triplets from the respective correspondence tables of the dyes producing the color of the respective pixel. An artificial image of the sample is then formed from the normalized RGB triplets for each dye as determined from the optimal combination. The artificial image thereby indicates a distribution of the respective dye over the sample image and facilitates determination of the amount of the corresponding molecular species. Associated methods, systems, and computer software program products are also provided.

82 Claims, 23 Drawing Sheets
(15 of 23 Drawing Sheet(s) Filed in Color)

U.S. PATENT DOCUMENTS

| | | | |
|---|---|---|---|
| 5,202,931 A | 4/1993 | Bacus | |
| 5,254,978 A * | 10/1993 | Beretta | 345/601 |
| 5,311,212 A * | 5/1994 | Beretta | 345/591 |
| 5,410,030 A * | 4/1995 | Yue et al. | 536/23.1 |
| 5,625,705 A | 4/1997 | Recht | |
| 5,732,150 A | 3/1998 | Zhou et al. | |
| 5,734,498 A * | 3/1998 | Krasieva et al. | 359/387 |
| 5,784,162 A | 7/1998 | Cabib et al. | |
| 5,835,617 A * | 11/1998 | Ohta et al. | 382/131 |
| 6,007,996 A | 12/1999 | McNamara et al. | |
| 6,010,841 A * | 1/2000 | Farid et al. | 430/583 |
| 6,025,137 A | 2/2000 | Shyjan | |
| 6,151,405 A | 11/2000 | Douglass et al. | |
| 6,276,798 B1 | 8/2001 | Gil et al. | |
| 6,330,349 B1 | 12/2001 | Hays et al. | |
| 6,373,615 B1 * | 4/2002 | Mann et al. | 359/241 |
| 6,409,770 B1 * | 6/2002 | Weiss et al. | 8/107 |
| 6,453,060 B1 | 9/2002 | Riley et al. | |
| 6,501,590 B1 * | 12/2002 | Bass et al. | 359/326 |
| 6,577,754 B1 | 6/2003 | Stone et al. | |
| 6,819,787 B1 * | 11/2004 | Stone et al. | 382/133 |
| 6,863,859 B1 * | 3/2005 | Levy | 264/401 |
| 2002/0063946 A1 * | 5/2002 | Bass et al. | 359/326 |
| 2003/0091221 A1 * | 5/2003 | Marcelpoil et al. | 382/128 |
| 2003/0096433 A1 * | 5/2003 | Meyer-Almes | 436/523 |
| 2003/0138140 A1 * | 7/2003 | Marcelpoil et al. | 382/162 |
| 2003/0176281 A1 * | 9/2003 | Hultgren | 503/204 |
| 2004/0047913 A1 * | 3/2004 | Allemann et al. | 424/490 |
| 2005/0065062 A1 * | 3/2005 | Roscoe et al. | 514/1 |

FOREIGN PATENT DOCUMENTS

| | | |
|---|---|---|
| WO | WO 98/55026 A1 | 12/1998 |

OTHER PUBLICATIONS

Duncan, et al., "Melastatin Expression and Prognosis in Cutaneous Malignant Melanoma", *Journal of Clinical Oncology*, 2001, pp. 568-576, vol. 19, No. 2.

* cited by examiner

| Index | R | G | B | Nb. Pixels |
|---|---|---|---|---|
| 0 | | | | $n_0$ |
| 1 | | | | $n_1$ |
| 2 | | | | $n_2$ |
| ... | ... | ... | ... | ... |
| 110 | 110 | 142 | 202 | $n_{110}+1$ |
| 111 | 245 | 222 | 388 | $n_{111}+2$ |
| 112 | | | | $n_{112}$ |
| 113 | | | | $n_{113}$ |
| ... | ... | ... | ... | ... |
| 252 | | | | $n_{252}$ |
| 253 | | | | $n_{253}$ |
| 254 | | | | $n_{254}$ |
| 255 | | | | $n_{255}$ |

900 →

=

| Index | R | G | B | Nb. Pixels |
|---|---|---|---|---|
| 0 | | | | $n_0$ |
| 1 | | | | $n_1$ |
| 2 | | | | $n_2$ |
| ... | ... | ... | ... | ... |
| 110 | 110 | 142 | 202 | $n_{110}+1$ |
| 111 | 124 | 111 | 202 | $n_{111}+1$ |
| 112 | | | | $n_{112}$ |
| 113 | | | | $n_{113}$ |
| ... | ... | ... | ... | ... |
| 252 | | | | $n_{252}$ |
| 253 | | | | $n_{253}$ |
| 254 | | | | $n_{254}$ |
| 255 | | | | $n_{255}$ |

DYE 1

DYE 2

+  →

DYE 1          DYE 2          DYE 1 + DYE 2

METHOD FOR QUANTITATIVE VIDEO-MICROSCOPY AND ASSOCIATED SYSTEM AND COMPUTER SOFTWARE PROGRAM PRODUCT

FIELD OF THE INVENTION

The present invention relates to image analysis and, more particularly, to a method for quantitative video-microscopy in cellular biology and pathology applications and an associated system and computer software program product therefor.

BACKGROUND OF THE INVENTION

Effective analysis of microscopic images is essential in cellular biology and pathology, particularly for detection and quantification of genetic materials such as, for example, genes or messenger RNA, or the expression of this genetic information in the form of proteins such as, for example, through gene amplification, gene deletion, gene mutation, messenger RNA molecule quantification, or protein expression analyses. Gene amplification is the presence of too many copies of the same gene in one cell, wherein a cell usually contains two copies, otherwise known as alleles, of the same gene. Gene deletion indicates that less than two copies of a gene can be found in a cell. Gene mutation indicates the presence of incomplete or non-functional genes. Messenger RNAs (mRNA) are molecules of genetic information, synthesized from a gene reading process, that serve as templates for protein synthesis. Protein expression is the production of a given protein by a cell. If the gene coding for the given protein, determined from a protein expression process, is enhanced or excess copies of the gene or mRNA are present, the protein may be over-expressed. Conversely, if the gene coding is suppressed or absent, the protein may be under-expressed or absent.

Normal cellular behaviors are precisely controlled by molecular mechanisms involving a large number of proteins, mRNAs, and genes. Gene amplification, gene deletion, and gene mutation are known to have a prominent role in abnormal cellular behaviors through abnormal protein expression. The range of cellular behaviors of concern includes behaviors as diverse as, for example, proliferation or differentiation regulation. Therefore, effective detection and quantification in gene amplification, deletion and mutation, mRNA quantification, or protein expression analyses is necessary in order to facilitate useful research, diagnostic and prognostic tools.

There are numerous laboratory techniques directed to detection and quantification in gene amplification, deletion and mutation, mRNA quantification, or protein expression analyses. For example, such techniques include Western, Northern and Southern blots, polymerase chain reaction ("PCR"), enzyme-linked immunoseparation assay ("ELISA"), and comparative genomic hybridization ("CGH") techniques. However, microscopy is routinely utilized because it is an informative technique, allowing rapid investigations at the cellular and sub-cellular levels while capable of being expeditiously implemented at a relatively low cost.

When microscopy is the chosen laboratory technique, the biological samples must first undergo specific detection and revelation preparations. Once the samples are prepared, a human expert typically analyzes the samples with a microscope alone in a qualitative study, or with a microscope coupled to a camera and a computer in a quantitative and generally standardized study. In some instances, the microscope may be configured for fully automatic analysis, wherein the microscope is automated with a motorized stage and focus, motorized objective changers, automatic light intensity controls and the like.

The preparation of the samples for detection may involve different types of preparation techniques that are suited to microscopic imaging analysis, such as, for example, hybridization-based and immunolabeling-based preparation techniques. Such detection techniques may be coupled with appropriate revelation techniques, such as, for example, fluorescence-based and visible color reaction-based techniques.

In Situ Hybridization ("ISH") and Fluorescent In Situ Hybridization ("FISH") are detection and revelation techniques used, for example, for detection and quantification in genetic information amplification and mutation analyses. Both ISH and FISH can be applied to histological or cytological samples. These techniques use specific complementary probes for recognizing corresponding precise sequences. Depending on the technique used, the specific probe may include a colorimetric (cISH) marker or a fluorescent (FISH) marker, wherein the samples are then analyzed using a transmission microscope or a fluorescence microscope, respectively. The use of a colorimetric marker or a fluorescent marker depends on the goal of the user, each type of marker having corresponding advantages over the other in particular instances.

In protein expression analyses, immunohistochemistry ("IHC") and immunocytochemistry ("ICC") techniques, for example, may be used. IHC is the application of immunochemistry to tissue sections, whereas ICC is the application of immunochemistry to cultured cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody.

In both hybridization and immunolabeling studies, chromagens of different colors are used to distinguish among the different markers. However, the maximum number of markers that may be used in a study is restricted by several factors. For example, the spectral overlapping of the colors used to reveal the respective markers may be a limiting factor because dyes may absorb throughout a large portion of the visible spectrum. Accordingly, the higher the number of dyes involved in a study, the higher the risk of spectral overlapping. Further, the spectral resolution of the acquisition device may be a limiting factor and the minimal color shift that the device is able to detect must be considered.

In addition, immunochemistry, as well as chemistry in ISH, are generally considered to exhibit poor sensitivity when quantification of a marker must be achieved. However, the quantification accuracy of these techniques may be dependent upon several factors. For instance, the type of reaction used may play a role in the accuracy of the technique since the linearity of the relationship between ligand concentration and the degree of the immunochemical staining reaction may strongly depend on the reaction type. More particularly, for example, a peroxidase/anti-peroxidase method may be more linear than a biotin-avidin method. The cellular localization of the markers may also affect accuracy where, for example, if membrane and nuclear markers spatially overlap, the resulting color is a mixture of the respective colors. Accordingly, since the corresponding quantification is subjective, the accuracy of the determination may be affected. In addition, a calibration standard such as, for example, cells with known features, gels with given concentrations of the marker, or the like, may be required where a developed analysis model is applied to a new and different case. Staining kits are generally available which incorporate calibration standards. However, the calibration standard is usually only applicable to a particular specimen, such as a specific cell or a structure of a specific type which is known to exhibit constant features with respect to the standard, and may be of limited utility when applied to a sample of a different nature.

Overall, the described "colorimetric" studies present sample analysis information in color and facilitate processing and quantification of the information to thereby help to provide a diagnosis or to form a prognosis of the particular case. For illustration, the detection and quantification of the HER2 protein expression and/or gene amplification may be assessed by different approaches used in quantitative microscopy. HER2 is a membrane protein that has been shown to have a diagnostic and prognostic significance in metastatic breast cancer. Because HER2 positive patients were shown to be more sensitive to treatments including Herceptin® (a target treatment developed by Genentech), the definition of the HER2 status of metastatic breast cancers has been proven to be of first importance in the choice of the appropriate treatment protocol. This definition of the HER2 status was based on a study of samples treated with either hybridization (FISH, ISH) or immunolabeling (IHC) techniques.

In such studies, using FISH with, for example, an FDA approved kit such as PathVysion® produced by Vysis, requires an image analysis protocol for counting the number of copies of the HER2 gene present in every cell. In a normal case, two copies of the gene are found in each cell, whereas more than three copies of the gene in a cell indicate that the gene is amplified. Alternatively, using IHC with, for example, an FDA approved kit such as Herceptest® produced by Dako, requires an image analysis protocol that classified the cases into four categories depending on the intensity and localization of the HER2 specific membrane staining. Current studies tend to show that these two investigation techniques (hybridization and immunolabeling) may be complementary and may help pathologists in tumor sub-type diagnosis when combined.

However, such colorimetry studies require extensive sample preparation and procedure control. Thus, when disposing of adapted staining protocols, it is critical to be able to verify that the staining for each sample matches the particular model used in the image acquisition and processing device such that useful and accurate results are obtained from the gathered information. Otherwise, the analysis may have to be repeated, starting again from the sample preparation stage, thereby possibly resulting in a costly and time-consuming process.

In a typical microscopy device based on image acquisition and processing, the magnified image of the sample must first be captured and digitized with a camera, prior to analysis. Further, in order to exploit the color properties of the sample, multispectral image acquisition devices and associated multispectral imaging methods have been developed, where such multispectral imaging is typically directed to acquiring multiple images of a scene at different spectral bands. More particularly, charge coupled device (CCD) digital cameras are typically used in either light or fluorescence quantitative microscopy. Accordingly, excluding spectrophotometers, two different techniques are generally used to perform such colorimetric microscopy studies. In one technique, a black and white (BW) CCD camera may be used. In such an instance, a gray level image of the sample is obtained, corresponding to a monochromatic light having a wavelength specific to the staining of the sample to be analyzed. The specific wavelength of light is obtained either by filtering a white source light via a specific narrow bandwidth filter, or by directly controlling the wavelength of the light source, using either manual or electronic controls. Accordingly, using this technique, the analysis time increases as the number of colors increases because a light source or a filter must be selected for every different sample staining or every different wavelength. Therefore, many different images of the sample, showing the spectral response of the sample at different wavelengths, must be individually captured in a sequential order to facilitate the analysis. When multiple scenes or fields of view must be analyzed, the typical protocol is to automate the sequence in a batch mode to conserve processing time.

According to a second technique, a color CCD digital camera is used, wherein three gray level images of the sample are simultaneously captured and obtained. Each gray level image corresponds to the respective Red, Green and Blue channel (RGB) of the color CCD camera. The images are then analyzed directly in the RGB color space by restricting the analysis to pixels located in a specific region of the RGB cube, the specific region also including pixels from a corresponding training database. Alternatively, the images are analyzed, after mathematical transform of the RGB color space, in one of the many color spaces defined by the CIE (International Commission on Illumination) such as, for example, an HLS (Hue, Luminance or Saturation) space. Alternatively, some camera manufacturers produce specific CCD cameras, wherein narrow bandwidth filters for targeting specific wavelengths may replace the usual Red, Green and Blue filters. In such an instance, the camera allows a fast image capture of the three spectral components of a scene in a parallel manner. However, cameras modified in this manner may be restricted to specific spectral analysis parameters because the filters cannot be changed and therefore cannot be adapted to address a unique dye combination used for the sample. Thus, the second technique generally relies upon either the detection of contrast between the species of interest and the remainder of the sample or the analysis of the sample over a narrow bandwidth.

Accordingly, techniques used in colorimetric analyses of prepared samples are of limited use in the detection and quantification of species of interest due to several factors such as, for example, spectral overlapping, mixing of colors due to spatial overlap of membrane, cytoplasmic, and nuclear markers, chromatic aberrations in the optical path, limited spectral resolution of the acquisition device, calibration particularities, subjectivity of the detection and quantification process, and inconsistencies between human operators. The image processing portion of colorimetric analysis techniques has historically been directed to the subjective detection of contrast within the prepared sample or to a complex and voluminous analysis of the sample at various specific wavelengths of light using a combination of light sources and filters.

Thus, there exists a need for a simpler and more effective colorimetric analysis technique that overcomes detection and quantification limitations found in prior art analysis techniques. Such a technique should also be capable of providing high quality data, comprising the necessary analysis information about the sample, while reducing subjectivity and inconsistency in the sample analysis.

SUMMARY OF THE INVENTION

The above and other needs are met by the present invention which, in one embodiment, provides a method of modeling a dye. First, a transmittance of a sample treated with the dye is determined from a color image of the treated sample. The image comprises a plurality of pixels and the transmittance is determined in each of a red, green, and blue channel of an RGB color space and for each pixel of the image so as to form an RGB triplet for each pixel. The RGB triplets are thereafter grouped according to the minimum transmittance in the red, green, and blue channels for the respective RGB triplet. Each group of RGB triplets is then normalized by summing the transmittances in each of the respective red, green, and blue channels and then dividing each of the summed transmittances by the number of RGB triplets in the respective group so as to form respective normalized RGB triplets. The normalized RGB triplets are then tabulated according to the minimum transmittance of each normalized RGB triplet so as to form a correspondence table for the dye, wherein the correspondence table extends in transmittance increments between 0% and 100% transmittance.

Another advantageous aspect of the present invention comprises a method of modeling a combination of a plurality of dyes in a video-microscopy system. First, a correspondence table is formed for each of the plurality of dyes. More particularly, a transmittance of a sample treated with the respective dye is determined from a color image of the treated sample. Each image comprises a plurality of pixels and the transmittance of the respective sample is determined in each of a red, green, and blue channel of an RGB color space and for each pixel of the image so as to form an RGB triplet for each pixel. The RGB triplets are then grouped according to the minimum transmittance in the red, green, and blue channels for the respective RGB triplet. Each group of RGB triplets is normalized by summing the transmittances in each of the respective red, green, and blue channels and then dividing each of the summed transmittances by the number of RGB triplets in the respective group so as to form respective normalized RGB triplets. Thereafter, the normalized RGB triplets are tabulated according to the minimum transmittance of each normalized RGB triplet so as to form the correspondence table for the respective dye, the correspondence table extending in transmittance increments between 0% and 100% transmittance. Once each correspondence table is determined, the correspondence tables of the plurality of dyes are orthogonally added so as to form a dye space representation of the plurality of dyes, wherein the dye space representation has one dimension for each dye and provides a reference model for a combination of the plurality of dyes.

Still another advantageous aspect of the present invention comprises a method of determining an amount of at least one molecular species comprising a sample from an image of the sample captured by a color image acquisition device, wherein each molecular species is indicated by a dye. First, a dye space representation of a plurality of dyes is formed, each dye having a corresponding correspondence table comprising a plurality of normalized RGB triplets. In order to form a correspondence table for a dye, a transmittance of a sample treated with the respective dye is determined from a color image of the treated sample. Each image comprises a plurality of pixels and the transmittance of the respective sample is determined in each of a red, green, and blue channel of an RGB color space and for each pixel of the image so as to form an RGB triplet for each pixel. The RGB triplets are then grouped according to the minimum transmittance in the red, green, and blue channels for the respective RGB triplet. Each group of RGB triplets is normalized by summing the transmittances in each of the respective red, green, and blue channels and then dividing each of the summed transmittances by the number of RGB triplets in the respective group so as to form respective normalized RGB triplets. Thereafter, the normalized RGB triplets are tabulated according to the minimum transmittance of each normalized RGB triplet so as to form the correspondence table for the dye, the correspondence table extending in transmittance increments between 0% and 100% transmittance. Once each correspondence table is determined, the correspondence tables of the plurality of dyes are then orthogonally added so as to form a dye space representation of the plurality of dyes, wherein the dye space representation has one dimension for each dye and provides a reference model for a combination of the plurality of dyes.

After the dye space representation is formed, each pixel of the image of the sample is compared to the reference model for the combination of the plurality of dyes, wherein the sample is treated by the combination of the plurality of dyes and each pixel has a color defined by an RGB triplet. From the comparison, an optimal combination of normalized RGB triplets is determined from the respective correspondence tables of the dyes producing the color of the respective pixel, wherein the normalized RGB triplets of the optimal combination are identifiable according to the respective dye. An artificial image of the sample, the artificial image corresponding to the sample image, may then be formed from the normalized RGB triplets for each dye determined from the optimal combination. The artificial image thereby indicates a distribution of the respective dye over the sample image and facilitates determination of the amount of the corresponding molecular species.

From the methods disclosed herein, it will be appreciated by one skilled in the art that other advantageous aspects of the present invention may comprise video-microscopy systems and associated computer software program products for implementing and accomplishing the described capabilities of such methods. For example, a video-microscopy system may comprises a color image acquisition device capable of capturing a magnified digital image of the sample and a computer device operably engaged with the image acquisition device for processing the captured image. Once the image is captured by the image acquisition device, the image may be balanced and normalized according to an empty field (white) reference and a black field image and, in some instances, corrected for shading. The image may also be corrected for chromatic aberrations on a channel by channel basis before the individual dyes are analyzed, various protocols are implemented, and histological samples stained according to those protocols are evaluated by the system according to the methods described herein. Accordingly, the computer device of such a system may comprise one or more processing portions configured to accomplish the appropriate analysis of captured images, the processing and storing of the data extracted therefrom, and the subsequent image processing and re-creation of various images utilized by the system. Further, an associated computer software program product is configured to be executable on such a computer device and may comprise one or more executable portions capable of accomplishing the methodology described herein, as will be further appreciated by one skilled in the art.

However, though embodiments of the present invention are described herein, for the sake of example, in terms of a video-microscopy system, it will be understood and appreciated by one skilled in the art that the concepts describe herein may have a broad applicability to non-microscopy systems. For instance, the concepts described herein may be applicable where one or more color components may be separately characterized such that useful information may be gleaned from the distribution of such color components with respect to an unknown sample comprising those color components. Further, though the methods, systems, and computer software program products of embodiments of the present invention are described herein in conjunction with an image acquisition device, it will be appreciated by one skilled in the art that such description is provided only for a convenient example of one embodiment of the present invention. For example, similar results may be obtained with embodiments wherein a system is configured to accept digital sample images previously captured or captured by an image acquisition device of a separate system.

Note also that, when such multi-spectral imaging techniques, as described herein, are particularly adapted to color imaging, substantially real time or video rate processing and viewing of the sample is facilitated. The use of, for example, a RGB color CCD camera allows acquisition and processing time for sample images to be performed at a video rate, typically 40 millisecond per frame, which provides a considerable advantage as compared to prior art imaging techniques which generally exhibit field of view acquisition and processing times of over 1 second. Where an RGB camera is used by the system, image acquisition through the different channels is performed in parallel and look-up tables (LUT) can be generated so as to map the spectral characteristics of each of various dyes. Thus, such capabilities may, for example, enhance processing speed and facilitate real time processing for display purposes. Accordingly, an a posteriori evaluation of the image can be performed to evaluate the efficiency of an a priori known dye combination model for each pixel. That is, an evaluation as detailed herein also provides a confidence evaluation for each pixel in that the color and intensity measured at the given pixel may be justified by a combination of the a priori known dyes.

Thus, embodiments of the present invention comprise a colorimetric analysis technique for prepared samples that provides effective detection and quantification of species of interest that overcomes limiting factors of prior art techniques such as, for example, spectral overlapping, mixing of colors due to spatial overlap of membrane and nuclear markers, limited spectral resolution of the acquisition device, calibration particularities, the subjectivity of the detection and quantification process, and inconsistencies between human operators of the analysis equipment. Embodiments of the present invention further provide an image processing technique which does not rely upon the subjective detection of contrast within the prepared sample or a complex and voluminous analysis of the sample at specific wavelengths of light using a combination of light sources and filters. Therefore, embodiments of the present invention provide a simpler and more effective colorimetric analysis technique that overcomes detection and quantification limitations in prior art analysis techniques, reduces subjectivity and inconsistency in the sample analysis, and is capable of providing the necessary analysis information about the sample, once an image of the sample is captured, without relying upon further examination of the sample to complete the analysis. These and other advantages are realized over prior art colorimetric analysis techniques as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
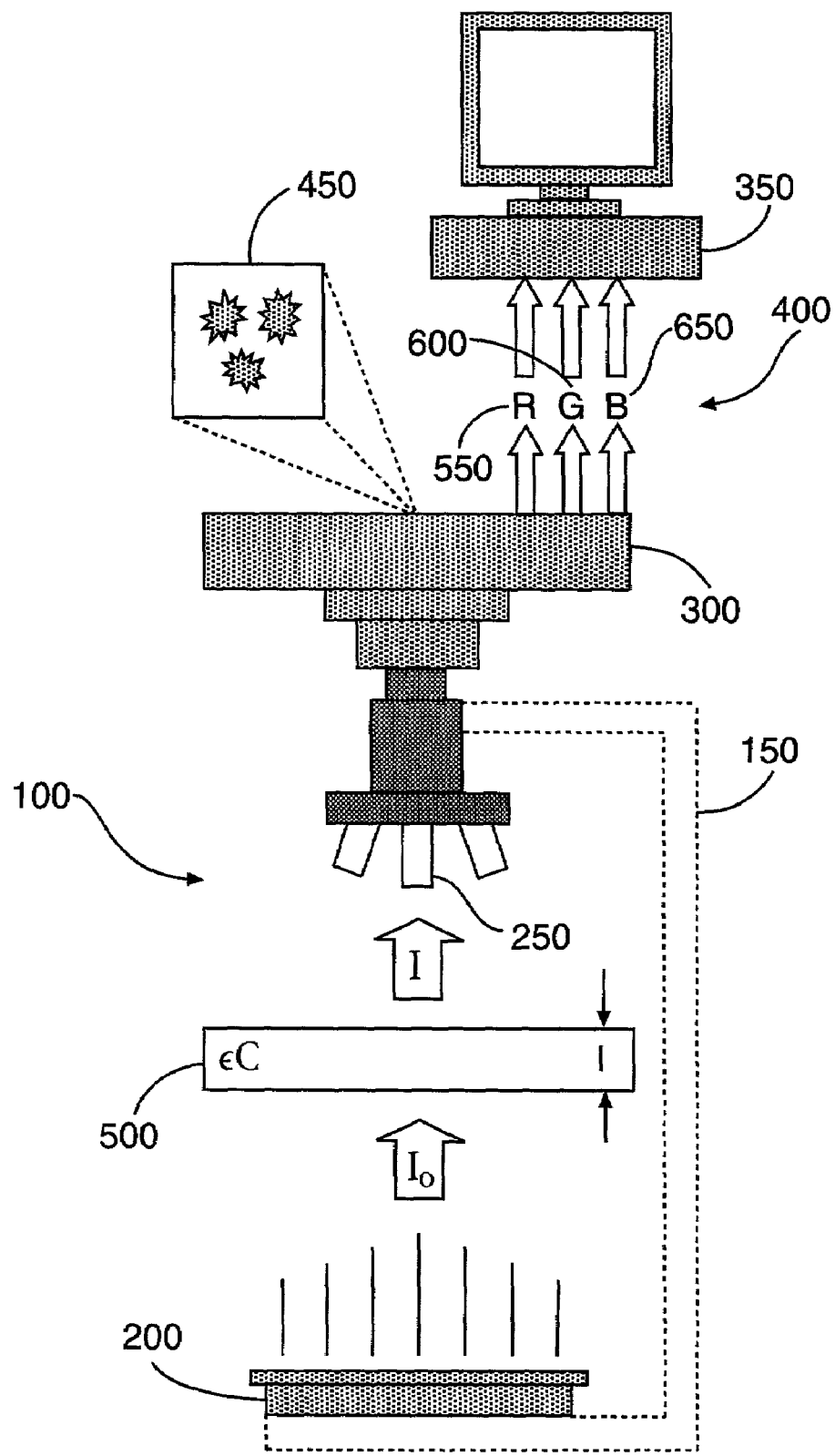

Having thus described the invention in general terms, reference will now be made to the accompanying drawings, which are not necessarily drawn to scale, and wherein:

FIG. 1 is a general schematic representation of a quantitative video-microscopy system according to one embodiment of the present invention.

Figure 2A:
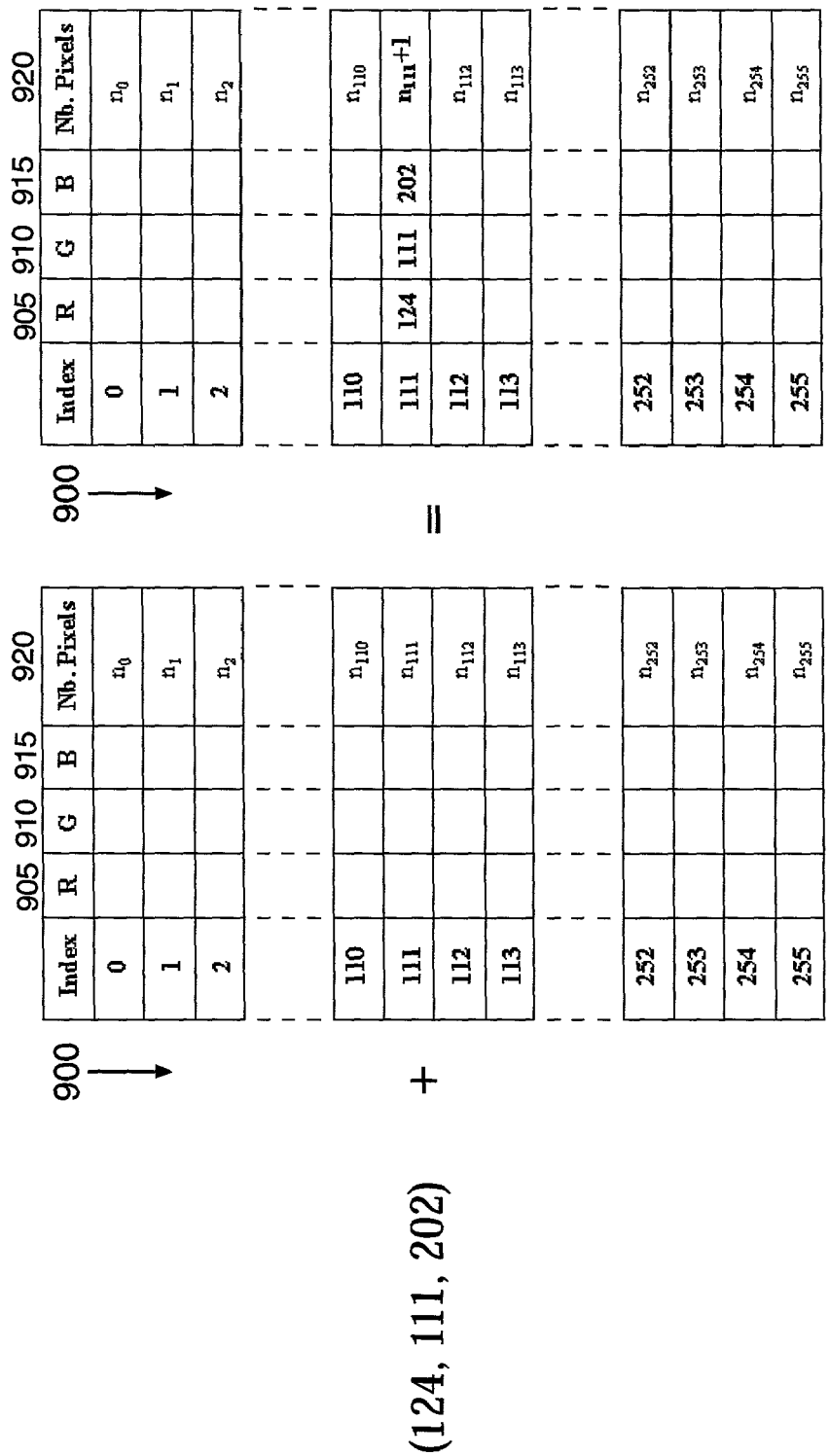
Figure 2B:
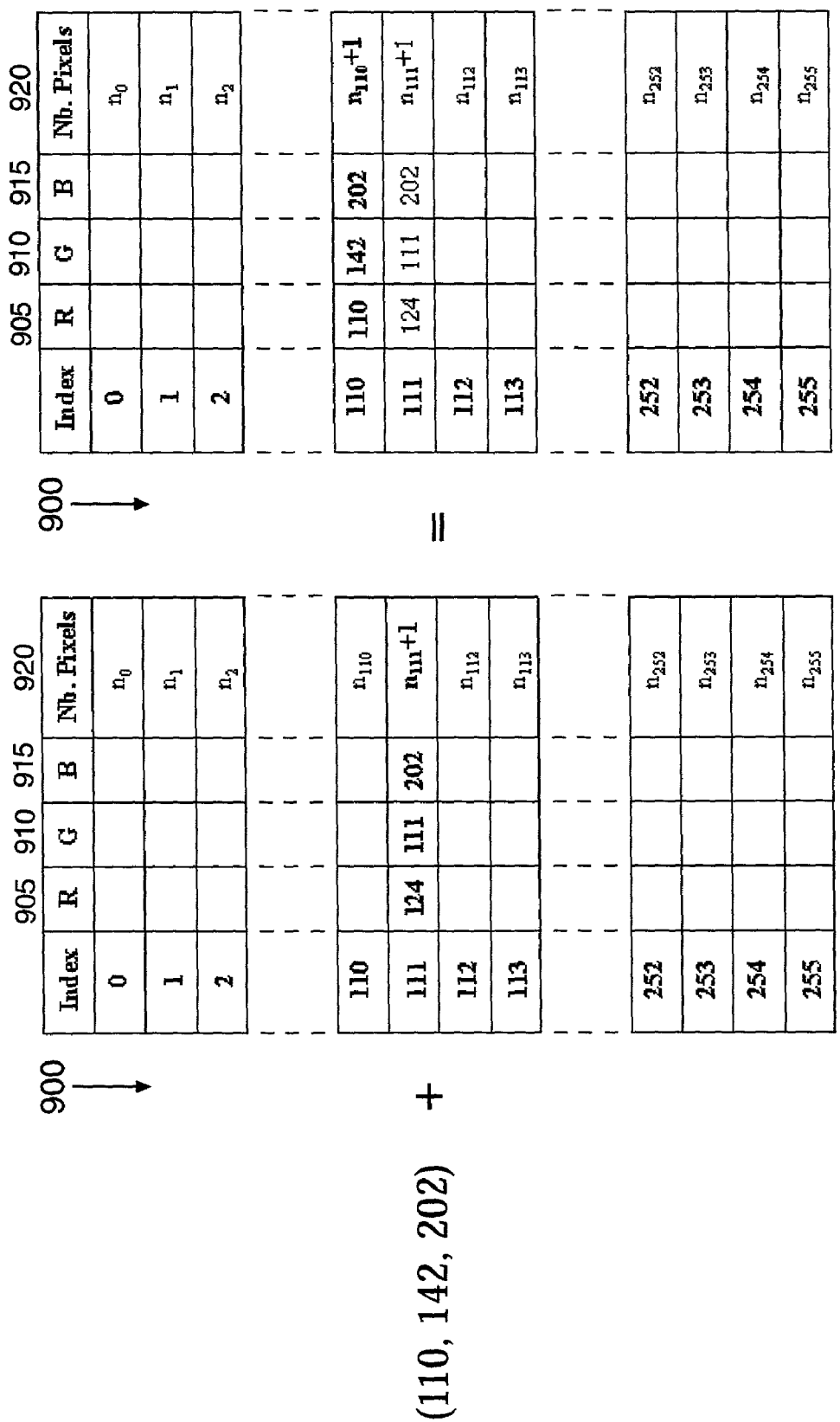

FIGS. 2A–2C schematically illustrate the addition of RGB triplets to a correspondence table for a dye according to one embodiment of the present invention.

Figure 3:
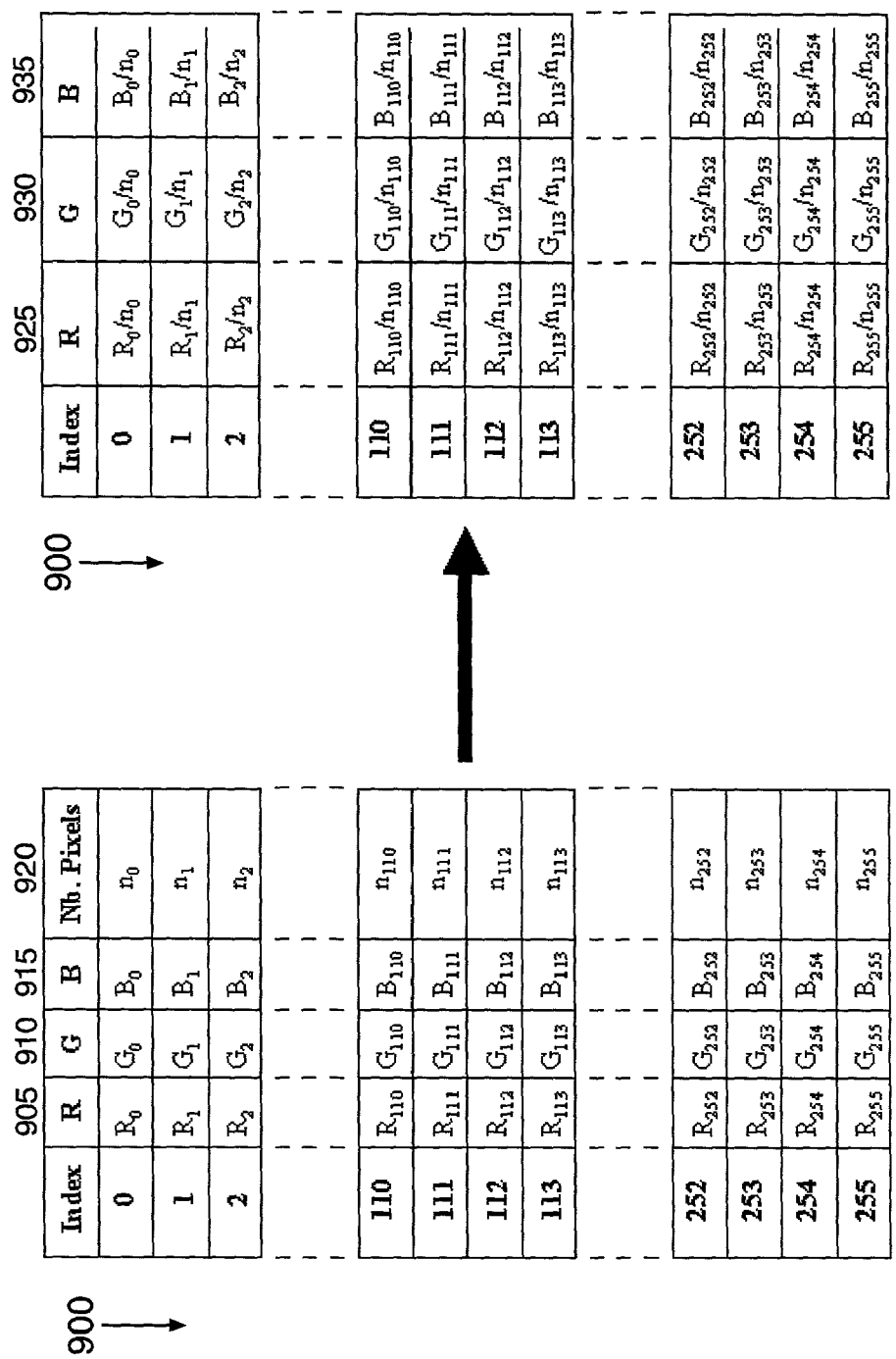

FIG. 3 schematically illustrates the normalization of a correspondence table according to one embodiment of the present invention.

Figure 4A:
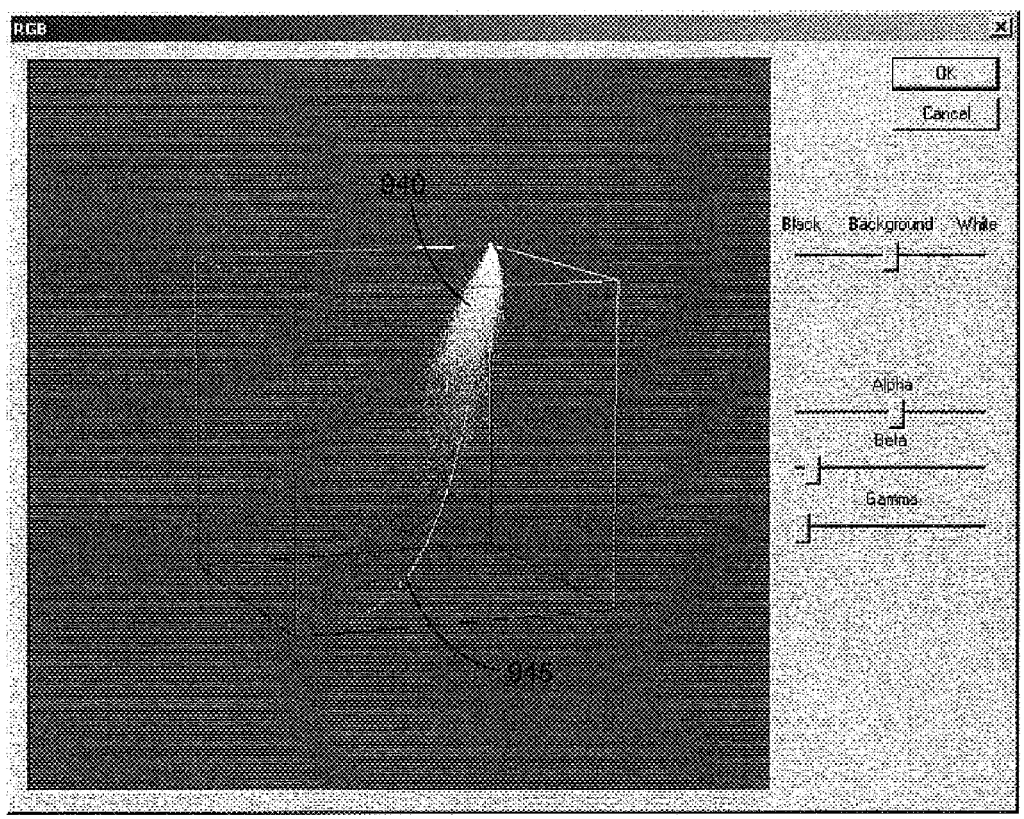

FIG. 4A illustrates an exemplary model of an NFR dye in a 3D RGB color space according to one embodiment of the present invention.

Figure 4B:
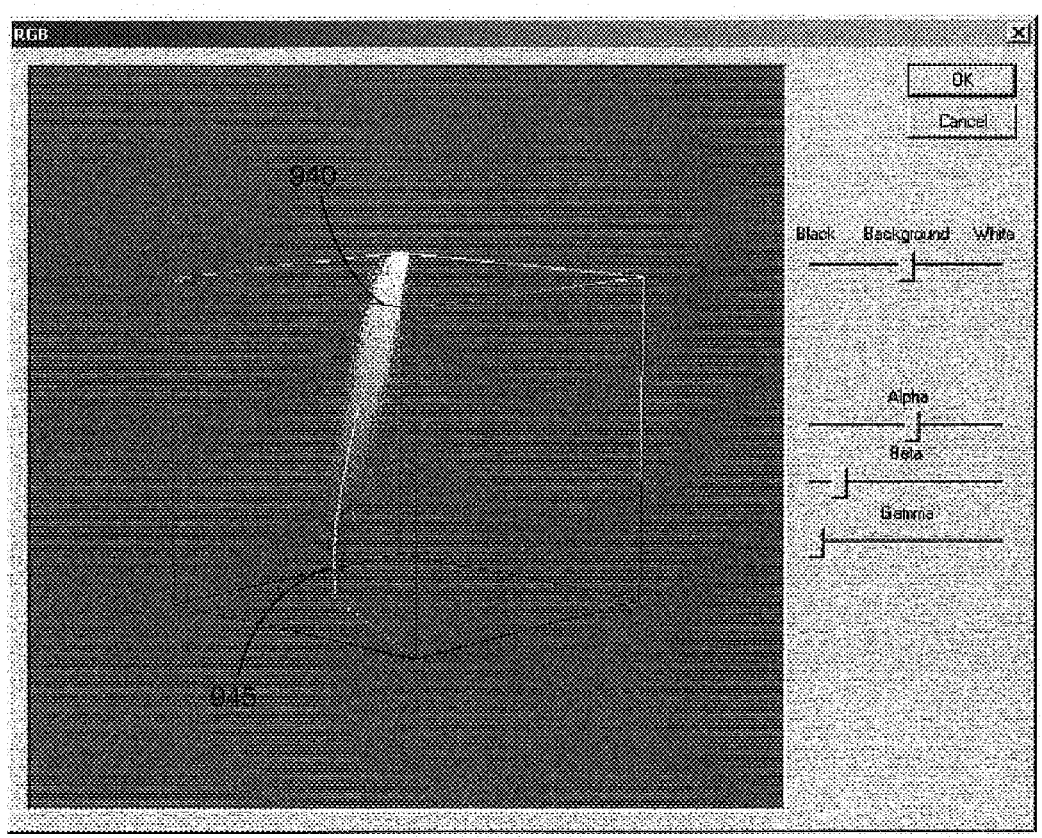

FIG. 4B illustrates an exemplary model of a BCIP-NBT dye in a 3D RGB color space according to one embodiment of the present invention.

Figure 4C:
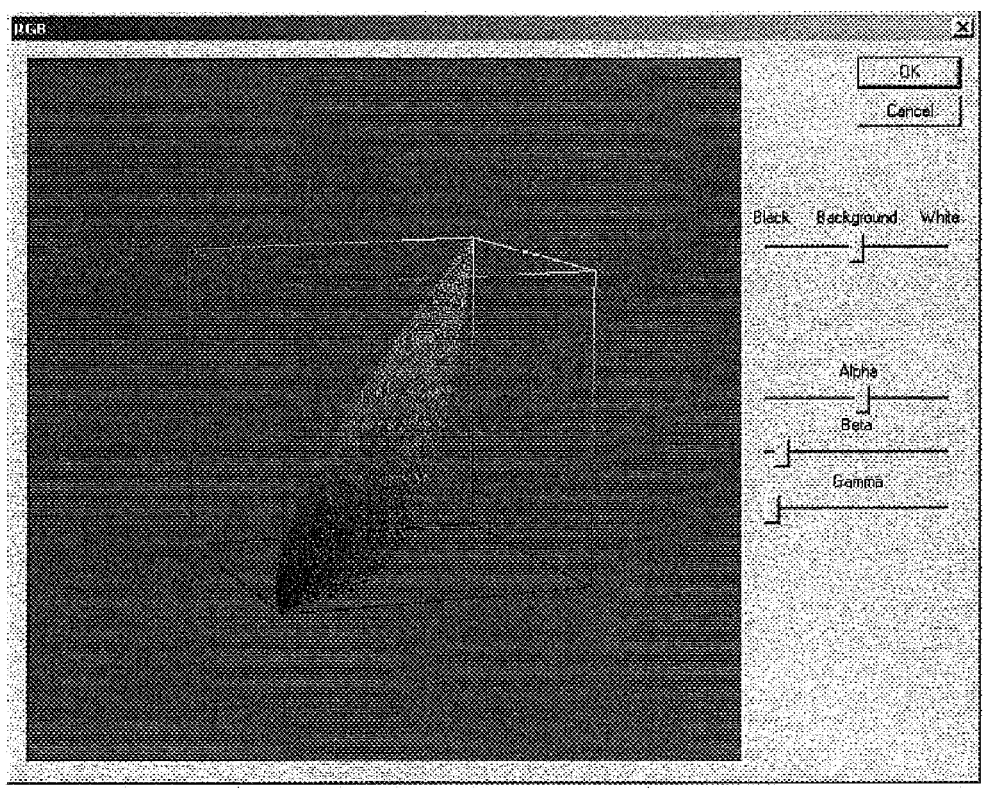

FIG. 4C illustrates an exemplary model of an NFR dye as shown in FIG. 4A combined with a BCIP-NBT dye as shown in FIG. 4B in a 3D RGB color space according to one embodiment of the present invention.

Figure 5A:

FIG. 5A illustrates an exemplary model of an NFR dye on a 1D scale (correspondence table) according to one embodiment of the present invention.

Figure 5B:

FIG. 5B illustrates an exemplary model of a BCIP-NBT dye on a 1D scale (correspondence table) according to one embodiment of the present invention.

Figure 5C:
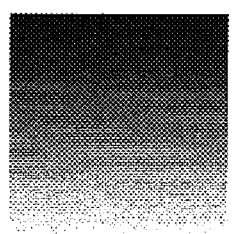
Figure 5C:
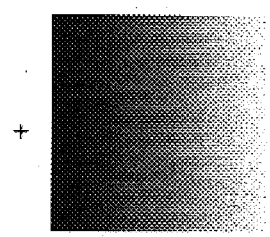
Figure 5C:
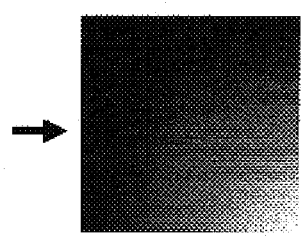

FIG. 5C illustrates an exemplary model of an NFR dye as shown in FIG. 5A combined by orthogonal addition with a BCIP-NBT dye as shown in FIG. 5B on a 2D scale (dye space) according to one embodiment of the present invention.

Figure 6:
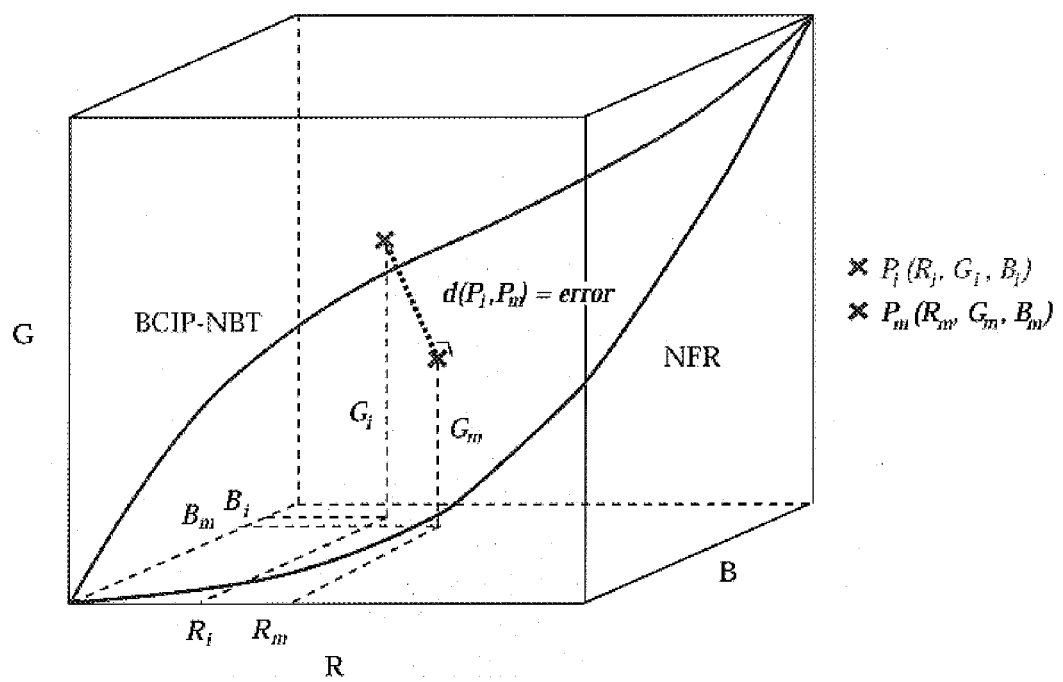

FIG. 6 is a schematic representation of a dye combination model plotted in a 3D RGB color space showing a pixel from an image of an unknown sample, stained according to the same protocol and plotted against the model, separated from the model by an error, according to one embodiment of the present invention.

Figure 7:
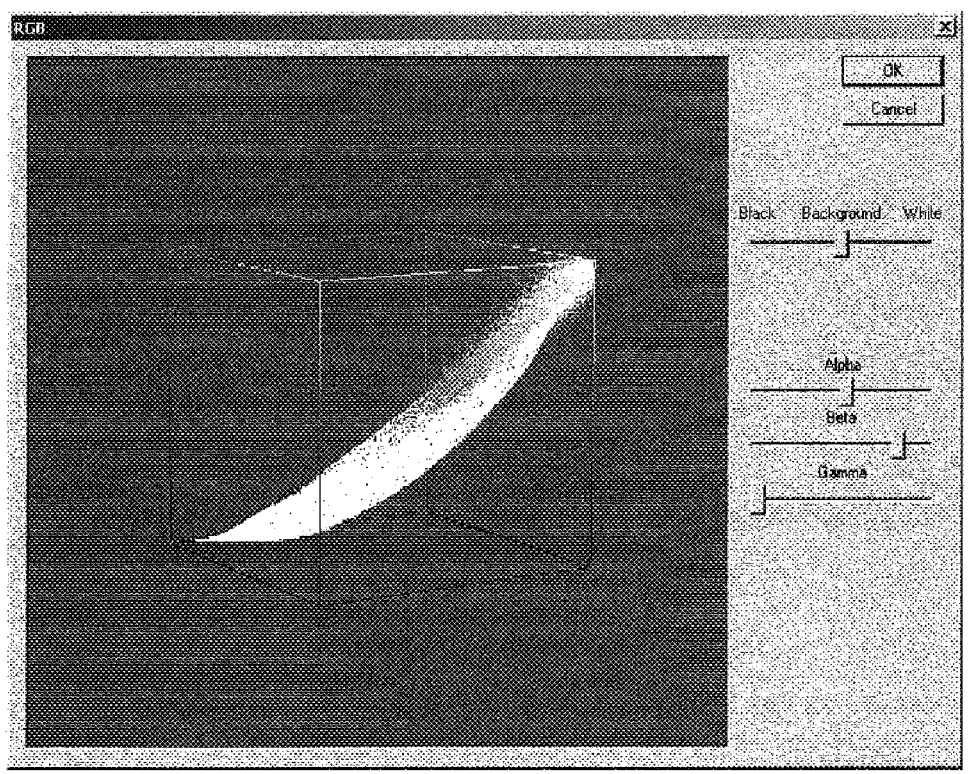

FIG. 7 illustrates an example of a dye combination model plotted in a 3D RGB color space having an overlaid plot of an image of an unknown sample stained according to the same protocol, according to one embodiment of the present invention.

Figure 8:
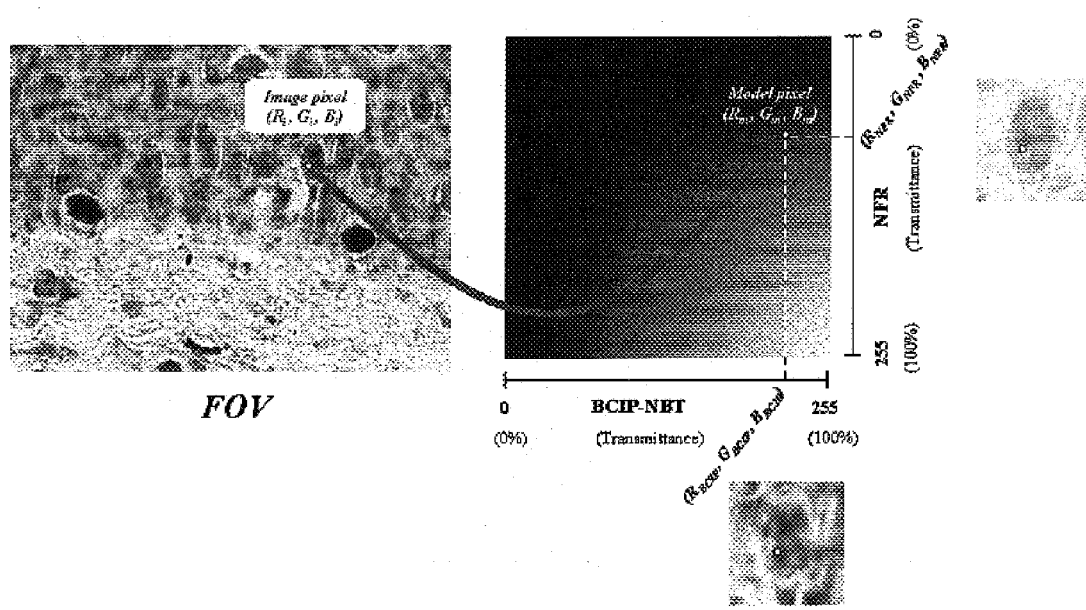

FIG. 8 illustrates an example of using a 2D scale (dye space) representation of a combination of two dyes to determine the color properties of a pixel of an image of an unknown sample stained according to the same protocol, according to one embodiment of the present invention.

Figure 9:
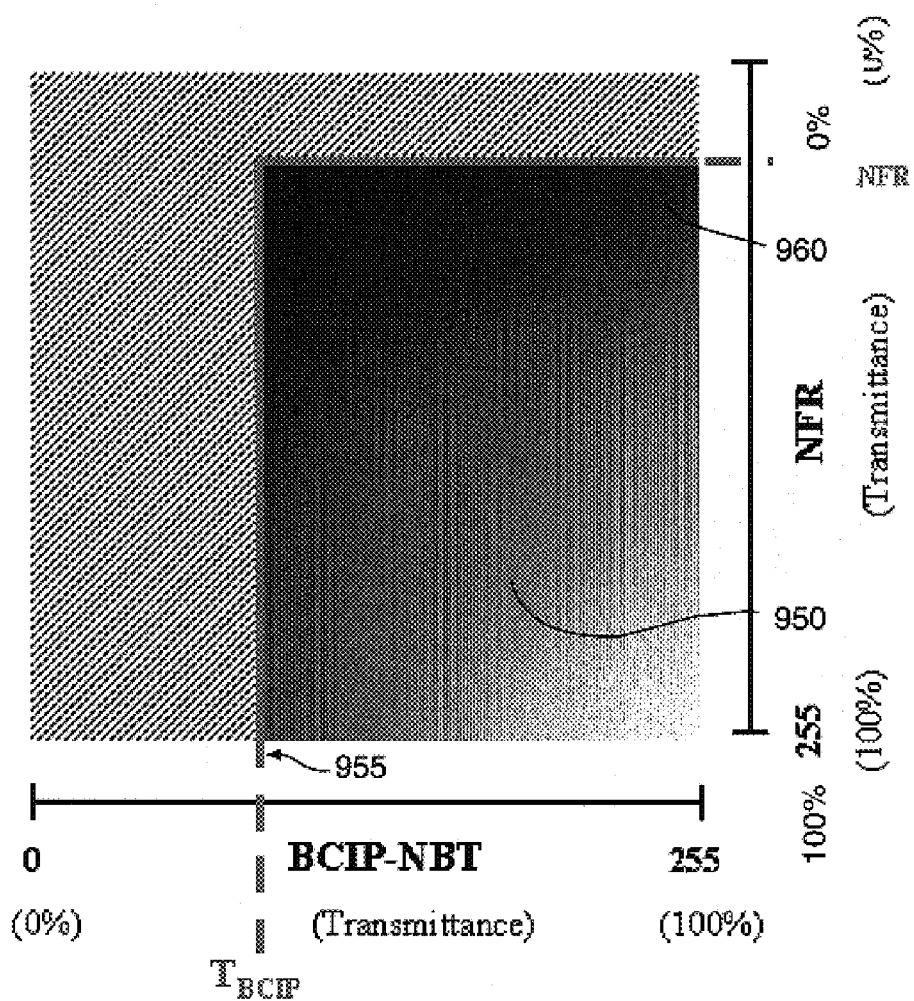

FIG. 9 is a schematic illustration of a 2D scale (dye space) representation of a combination of two dyes having a defined bounded region in which a search is conducted for an optimal combination for a pixel of an image of an unknown sample stained according to the same protocol, according to one embodiment of the present invention.

Figure 10:
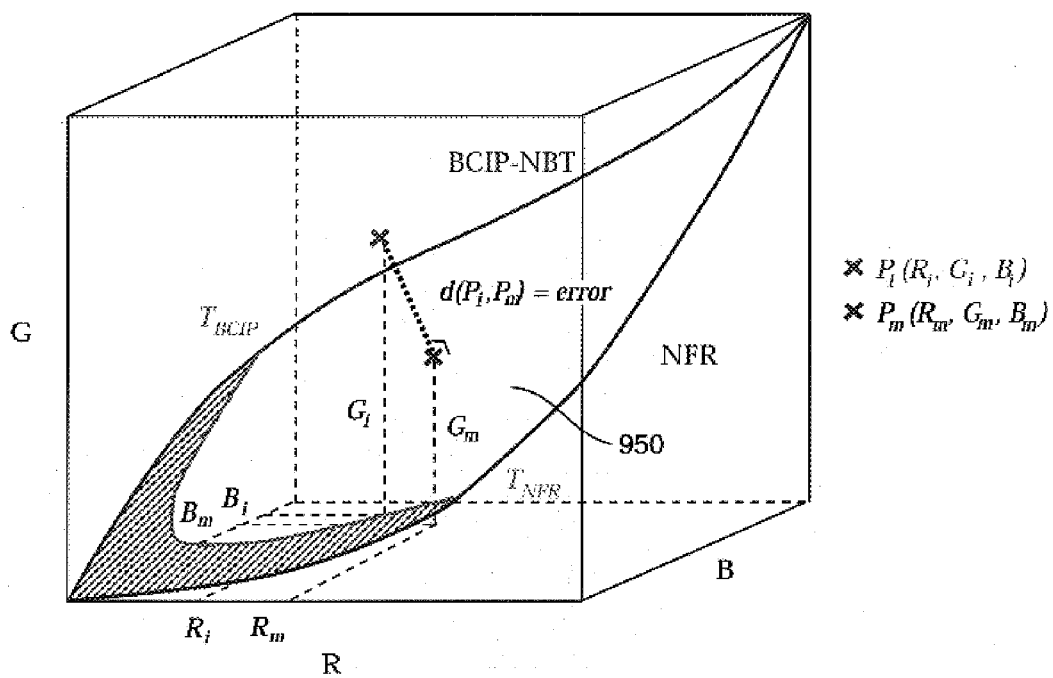

FIG. 10 is a schematic illustration of a 3D RGB color space representation of a combination of two dyes having a defined bounded region in which a search is conducted for an optimal combination for a pixel of an image of an unknown sample stained according to the same protocol, according to one embodiment of the present invention.

Figure 11A:
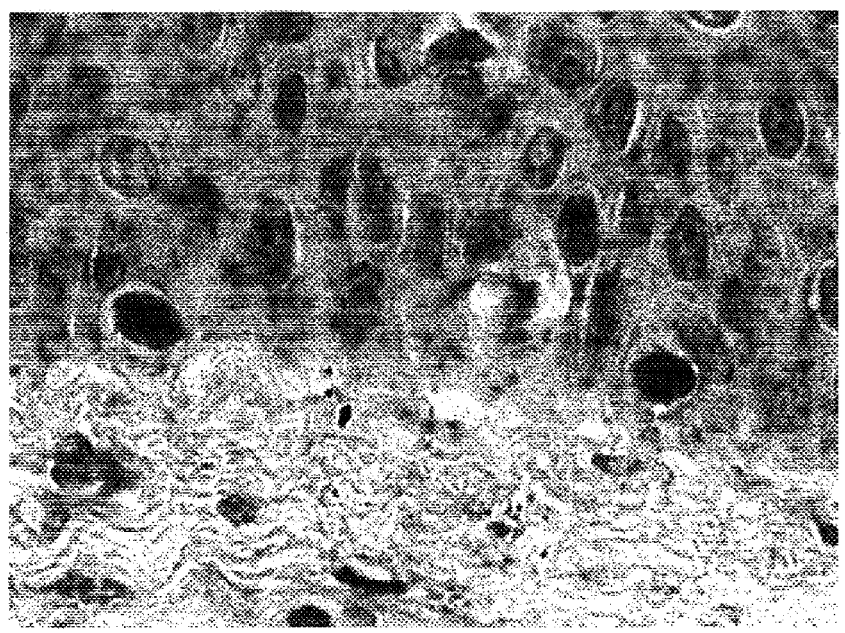

FIG. 11A is an image of an unknown sample stained with a combination of NFR and BCIP-NBT according to one embodiment of the present invention.

Figure 11B:
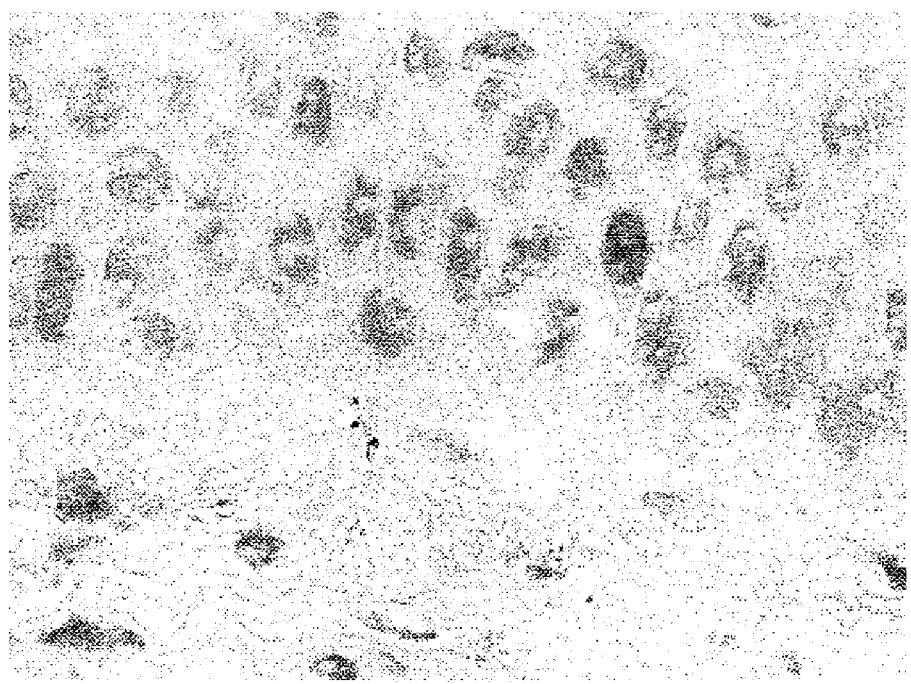
Figure 11C:
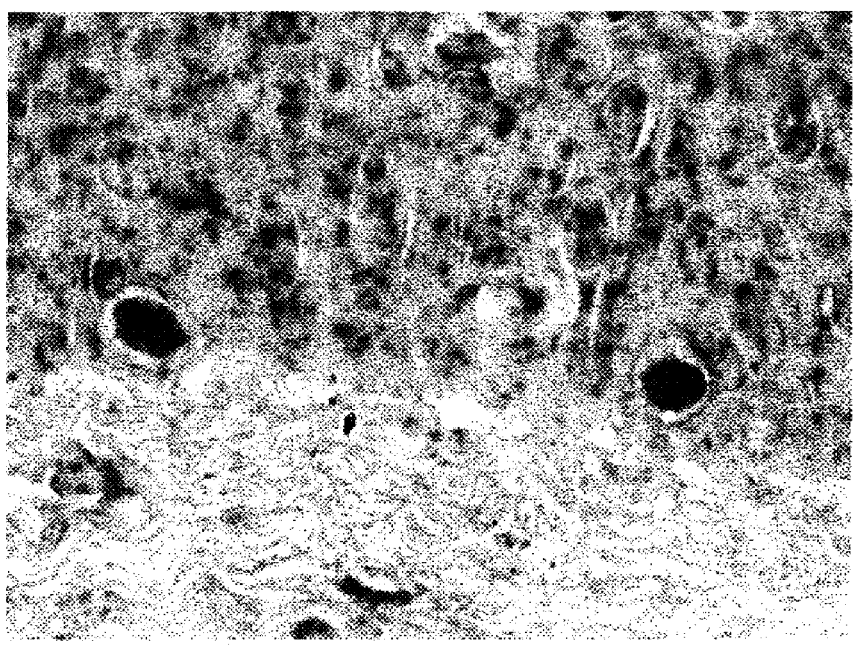

FIGS. 11B and 11C are images of the unknown sample of FIG. 11A showing only the NFR dye component and only the BCIP-NBT dye component, respectively, according to one embodiment of the present invention.

Figure 11D:
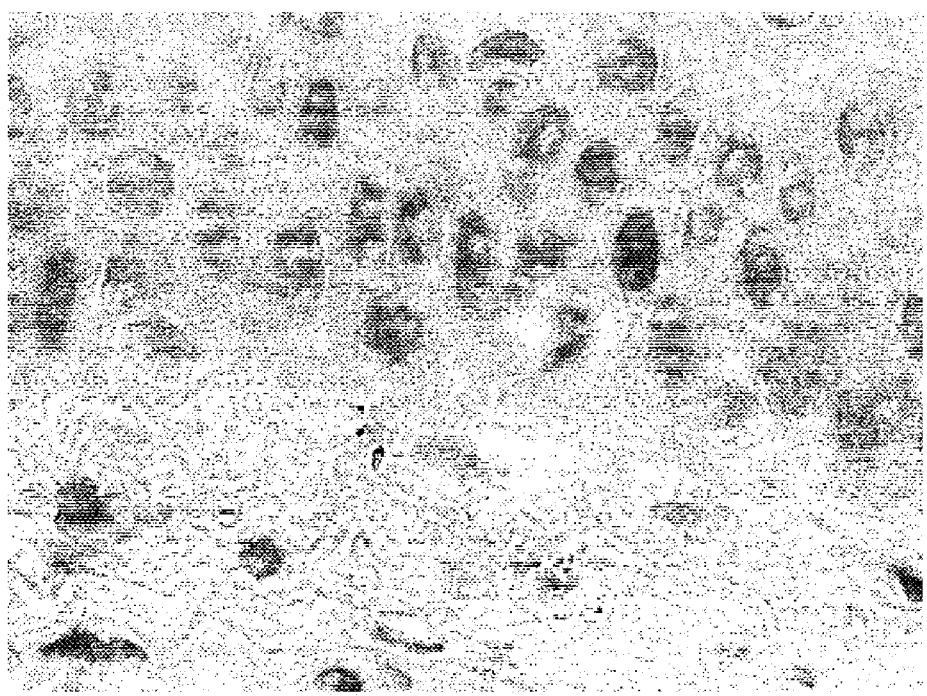
Figure 11E:
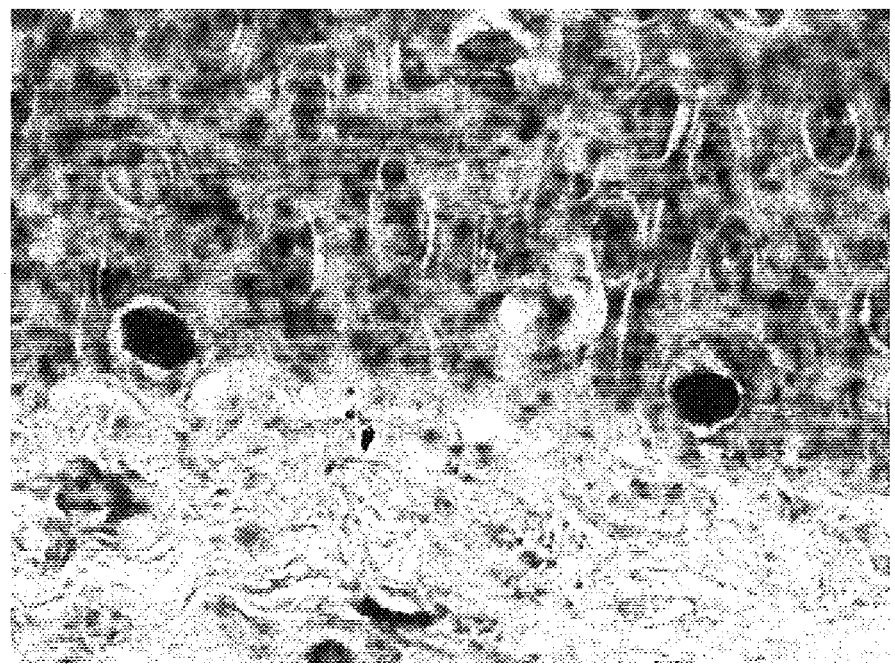

FIGS. 11D and 11E are images of the unknown sample of FIG. 11A showing only the gray level NFR dye component and only the gray level BCIP-NBT dye component, respectively, according to one embodiment of the present invention.

Figure 12:
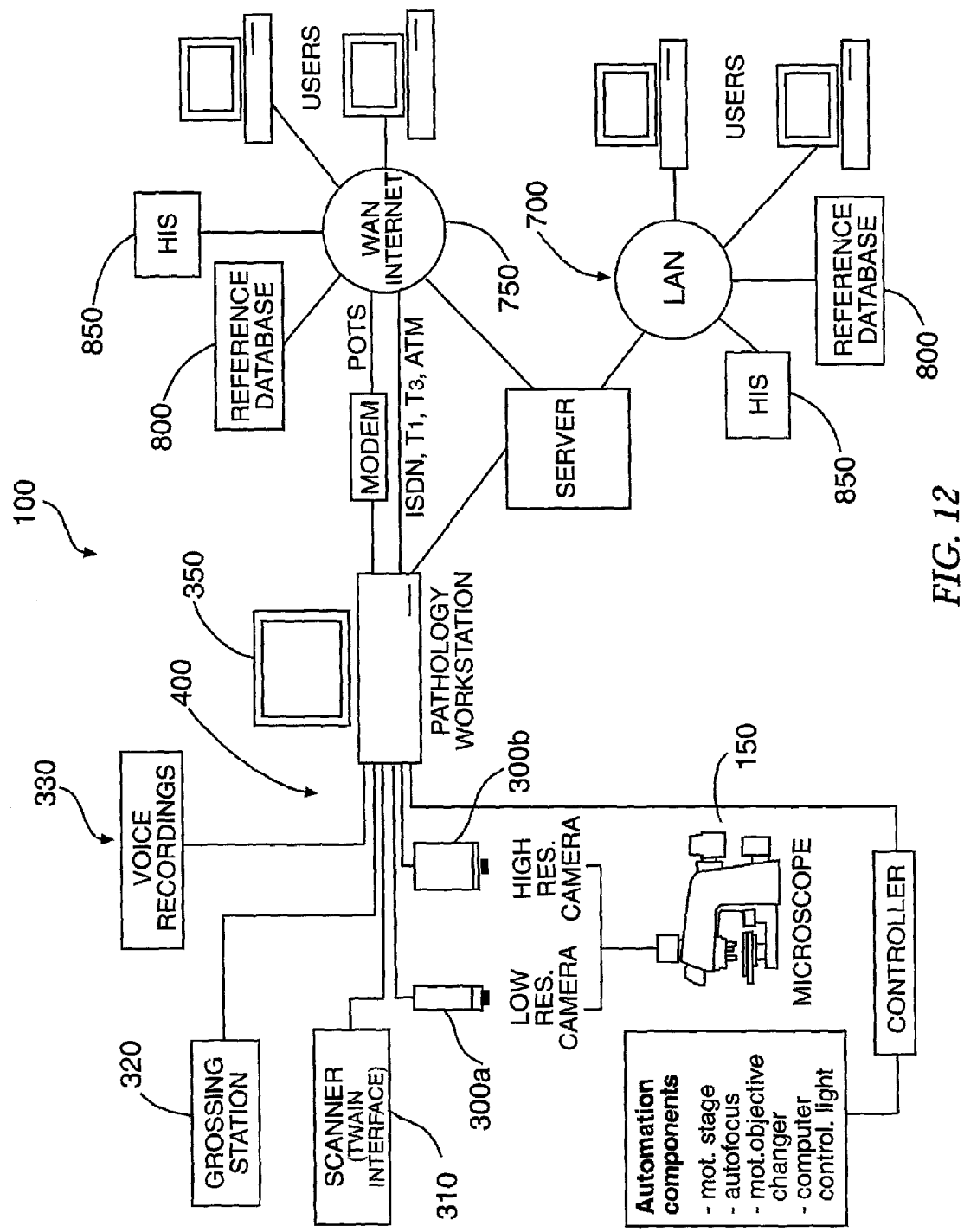

FIG. 12 is a schematic representation of the practical realization in an extended configuration of a quantitative video-microscopy system according to one embodiment of the present invention.

Figure 13A:
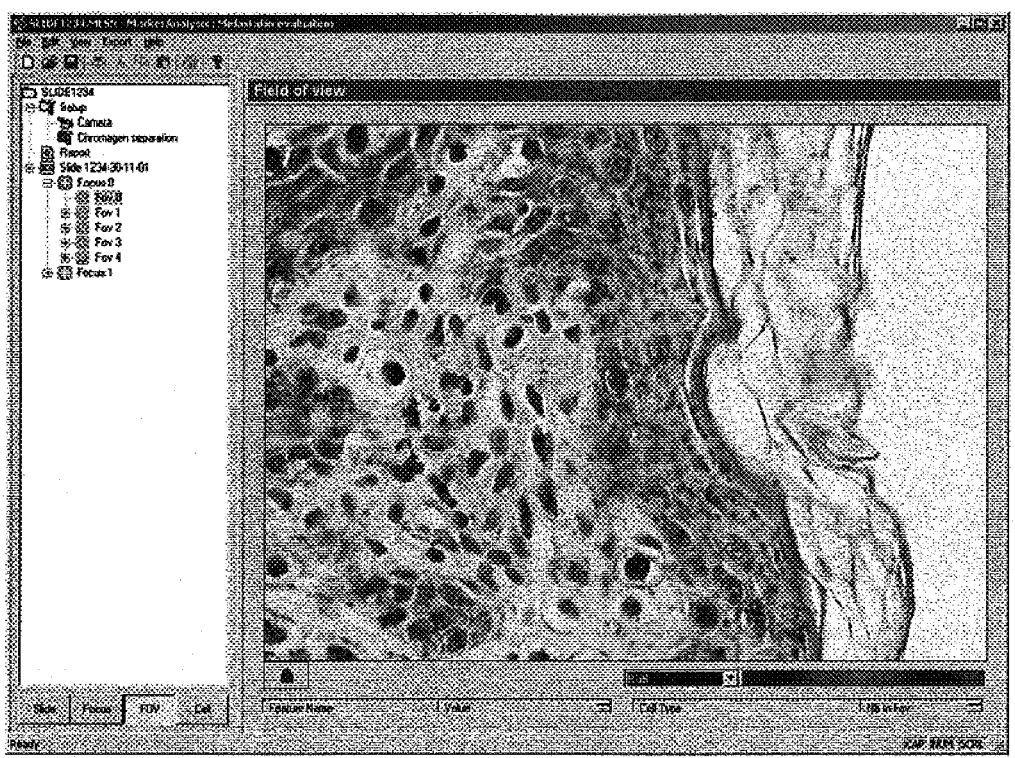

FIG. 13A is an image of an unknown sample stained with a combination of NFR and BCIP-NBT according to one embodiment of the present invention and illustrating an unknown component.

Figure 13B:
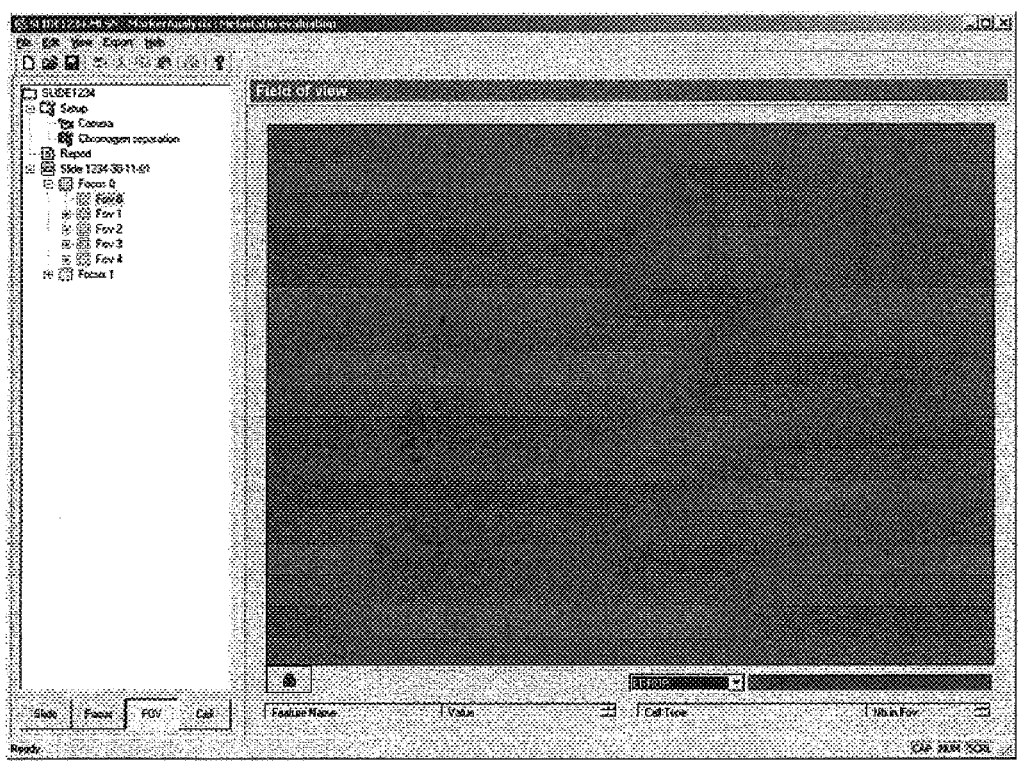

FIG. 13B is an image of a per pixel error distribution of the error between the image as shown in FIG. 13A and the two dye model (NFR and BCIP-NBT) according to one embodiment of the present invention.

Figure 13C:
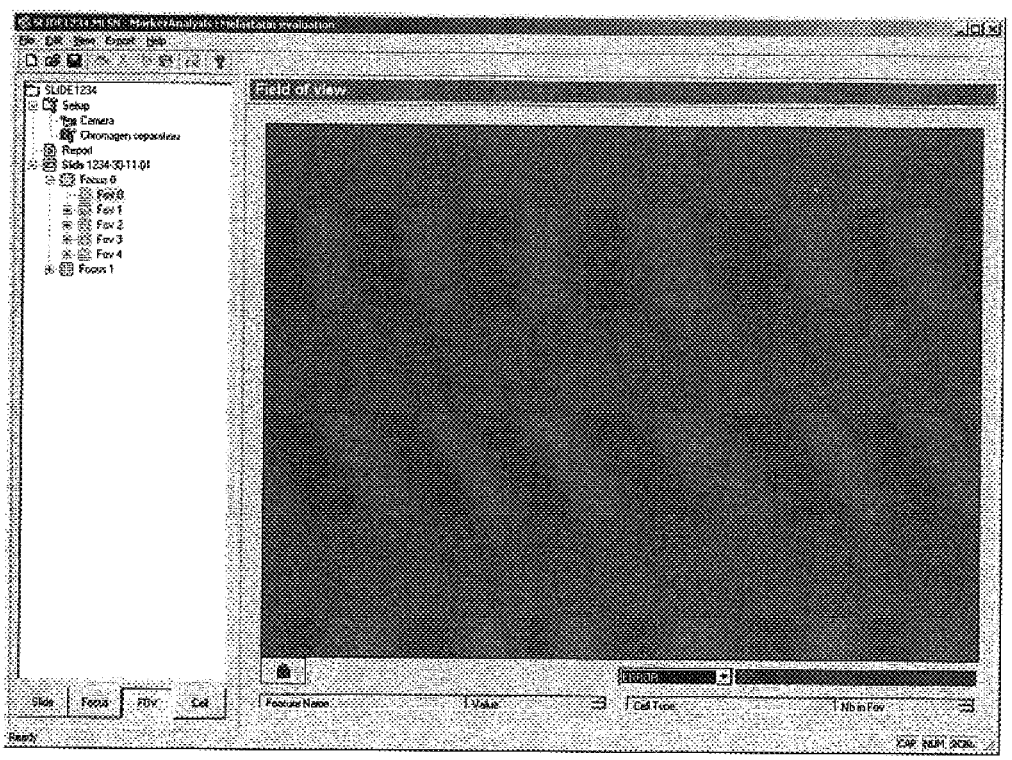

FIG. 13C is an image of a per pixel error distribution of the error between the image as shown in FIG. 13A and a three dye model (NFR, BCIP-NBT, and melanin) according to one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Probably the most rapidly increasing cancer appears to be cutaneous melanoma, for which a new marker has recently been discovered. However, diagnostic and prognostic use requires the precise quantification of the downregulation of this marker in tumor melanocytes. As such, multispectral analysis is one of the most reliable colorimetric methodologies for addressing this quantification in routine bright field microscopy. Accordingly, a technique dedicated to the optimization of multispectral analysis and application thereof to the quantification of the melanoma marker is described herein, along with associated systems and computer software programs. More particularly, the present invention is described herein as being applied to the quantification of the melastatin marker, a promising cutaneous melanoma tumor marker, though it will be understood that the particular application is presented for exemplary purposes only and is not to be construed as a restriction or limitation on the applicability of the present invention. Accordingly, the present invention may be more generally applicable to quantitative colorimetric studies of a wide range of samples stained by one or more dyes and analyzed according to the methods described herein.

According to the American Cancer Society, the incidence of cutaneous melanoma is increasing more rapidly than any other cancer in the United States. For example, there will be about 51,400 new cases of melanoma in 2001, 29,000 men and 22,400 women, which is about a 9% increase from 2000. In 2001, at current rates, about 1 in 71 Americans will have a lifetime risk of developing melanoma. Generally, surgical excision of localized primary cutaneous melanoma (American Joint Committee on Cancer [AJCC] stages I and II, comprising approximately 75% of diagnoses) may lead to cure in many patients. Further, the overall 5-year survival rate for the patients having surgical excision is approximately 80%, thereby suggesting that approximately 20% of stage I and II patients may have micrometastatic disease at the time of cutaneous melanoma diagnosis. Melanoma is one of the most lethal of cancers. For example, in 1996, melanoma accounted for approximately 2% of all cancer-related deaths in the United States. Currently, there is no cure for patients having melanoma that has metastasized to distant sites, and the median survival of such patients is only approximately 6 months. Therefore, according to Duncan et al., *J. Clin. Oncol.*, Vol. 19, No. 2, pp. 568–576, 2001, the contents of which are incorporated herein by reference, identifying patients at high risk of developing metastases is one of the most critical issues in the management of this form of cancer.

A novel gene, named melastatin, whose expression correlates with in vivo aggressiveness, has been discovered in murine B16 melanoma cell sublines with divergent metastatic potential in vivo using differential mRNA analysis. The human melastatin has been cloned and is generally designated as MLSN-1. Northern blot analysis has demonstrated melastatin expression only in melanocytic cells and the choroid (eye tissue), while no expression of melastatin in other tissues was detected. Though in situ hybridization analysis of human cutaneous melanocytic tissues revealed that melastatin mRNA was uniformly expressed in benign melanocytic nevi, primary cutaneous melanomas showed variable expression of melastatin mRNA. Notably, melastatin status was correlated with the thickness of the primary tumor, according to Deeds et al., *Hum. Pathol.*, Vol. 31, No. 11, pp. 1346–1356, 2000, the contents of which are incorporated herein by reference. Preliminary data has also suggested that melastatin expression is inversely associated with human metastatic disease. However, most recent results indicate that downregulation of melastatin mRNA in the primary cutaneous tumor is a prognostic marker for metastasis in patients with localized malignant melanoma and is independent of tumor thickness and other variables. When used in combination, melastatin status and tumor thickness allow for the identification of subgroups of patients at high and low risk of developing metastatic disease.

U.S. Pat. No. 6,025,137 is related to the Melastatin™ gene and metastatic melanoma and, more particularly, is directed to methods of detecting Melastatin™ in patient tissue samples in order to determine whether a patient has, or is at risk for developing, metastatic melanoma. In order to use Melastatin™ expression as a diagnostic marker in routine work, evaluation must be conducted with reliability and at low cost. IHC and ISH on histological material from skin samples are typically the most convenient techniques that are routinely used to quantify protein expression at low cost.

Thus, embodiments of the present invention are directed to the quantification of melastatin staining in both normal melanocyte nuclei (melanocytes from the basal layer of epithelial cells), considered as reference nuclei, and abnormal melanocyte nuclei (melanocytes from tumor foci). The results of such a quantitative analysis indicate whether the gene is either downregulated or normally expressed in the abnormal nuclei. However, the efficiency of the quantitative analysis heavily depends upon the image analysis methodology, which must consider and perform segmentation of the melanocyte nuclei, as well as colorimetric analysis of the specific dyes used in the protocol.

The platform for the evaluation of biological samples via image analysis is increasingly shifting from a general-purpose image analyzer to a more, and often highly, specialized dedicated "pathology workstation." Such workstations are typically designed to facilitate routine work, often combining many of the tools needed to provide a pathologist with the necessary information to determine the best possible results. One example of such a workstation is illustrated in FIG. 1 as a quantitative video-microscopy system, indicated by the numeral 100, according to one embodiment of the present invention. The system 100 generally comprises a microscope 150 having a light source 200 and a magnifying objective 250, a camera 300, a computer device 350, and a data transmission link 400 between the camera 300 and the computer device 350. The microscope 150 may comprise, for example, an Axioplan (or Axiovert) microscope produced by ZEISS of Germany or a similar microscope having a bright field light source. The camera 300 operably engages the microscope 150 and, in one embodiment, comprises a 3CCD RGB camera such as, for instance, a Model No. DC-330E Dage-MTI RGB 3CCD camera produced by Dage-MTI, Inc. of Michigan City, Ind. or a similar RGB camera. Typically, such a camera 300 also includes an associated frame grabber (not shown) to facilitate image capture, both the camera 300 and associated frame grabber being referred to herein as the "camera 300" for convenience. In some instances, both camera 300 and microscope 150 may be replaced by, for example, a linear flat scanner having a 3CCD chip or equivalent and a controlled illumination source. For instance, a Model No. Super CoolScan 4000 ED scanner produced by Nikon Corporation may be used for low-resolution imaging. Note that, though different configurations of the necessary system 100 are contemplated by the present invention, the present invention will be described herein in terms of a camera 300 and associated microscope 150. Accordingly, one skilled in the art will understand and appreciate the capabilities and methodologies associated with these different configurations for accomplishing the present invention as detailed herein.

The camera 300 is generally configured to capture an image 450 of a sample 500 through the magnifying objective 250 (where a flat scanner is used, the image 450 is captured through internal lenses), wherein the image 450 may further comprise a digital image having corresponding image data (collectively referred to herein as "the image 450"). The image 450 is generally captured as a whole, wherein the corresponding image data comprises a red channel 550, a green channel 600, and a blue channel 650 image of the field of view. The data transmission link 400 is configured so as to be capable of transmitting the image 450 to the computer device 350, wherein the computer device 350 is further configured to be capable of analyzing the image 450 with respect to each of the red 550, green 600, and blue 650 channels.

The quantitative video-microscopy system 100 of the present invention, when evaluating a melastatin expression, must meet certain requirements in order to provide usable results, as will be described in further detail herein. For example, staining of thick histological samples may induce non-linearity in the relationship between the intensity of the staining and the protein concentration in the sample. In such an instance, the integrated optical density of the sample will not provide stable, reproducible colorimetric data and thus an alternative measure must be used. In addition, 3 chromagens are generally present in the histological samples: the marker (BCIP-NBT), a morphological counterstain (Nuclear Fast Red—NFR), and natural melanin. All three chromagens must be taken into account for several reasons. First, in order to realize a quantitative analysis of the tumor marker when using a counterstain for morphological analysis and melanocyte recognition, a specific spectral analysis is required in order to distinguish and quantify both the marker and the counterstain. Further, where the counterstain is applied to the sample after the marker, cells highly stained with the marker are less easily stained by the counterstain. Also, melastatin is used as a downregulation marker and, because of high background noise, it is often problematic to discriminate non-specific background noise from downregulated marker specific staining. In addition, melanin (brown) may also be a potential source of interference during evaluation of the marker in regions of particularly intense staining.

Thus, according to one advantageous aspect of the present invention, a spectral analysis of the melastatin expression is based on computation of a model of each dye used in the protocol. As previously described, in a melastatin expression, three distinct spectral components are typically involved: the counterstain (NFR); the melastatin marker (BCIP-NBT); and a natural pigment (melanin) of the histological sample. Accordingly, the spectral properties of each of the different spectral components are first studied separately with the video-microscopy system 100 of the present invention using, for example, one histological slide per dye. That is, in the training phase of the video-microscopy system 100, it is presumed that if only one dye is being analyzed by the system 100, then the dye will be homogeneously and continuously distributed in an RGB color space. Once the histological sample 500 for a particular dye is prepared, an image 450 of the sample 500 is captured with the camera 300 through the magnifying objective 250. The resulting digital image 450 is an ordered two-dimensional (2D) set of pixels, wherein each pixel is defined by an RGB triplet. That is, if an 8 bit color image acquisition device such as, for example, an 8 bit 3CCD RGB camera 300 is utilized, each pixel may be defined by a measured light intensity I or transmittance of the sample 500 in each of the red 550, green 600, and blue 650 channels, the measured light having 256 possible values ranging between limits of 0 and 255.

When at least one image 450 of a histological sample 500 for each dye has been captured, then artificial images for each dye in a separate unknown sample, stained according to the same protocol, may be reconstructed, as will be discussed in further detail below. Typically, the image 450 of the histological sample 500 for each dye is analyzed by the computer device 350 on a per pixel basis so as to provide a corresponding data set of RGB triplets. An RGB color space may then be established, the RGB color space comprising a cube having an axis for each of the red 550, green 600, and blue 650 channels, with each axis extending from 0 to 255 for an 8 bit image acquisition device 300. Accordingly, it has been found that, when the RGB triplets are plotted in the RGB color space to illustrate the spatial distribution of the dye within that space, the dye occupies a characteristic path leading from black (0% transmittance or no intensity in each of the red 550, green 600, and blue 650 channels) to white (100% transmittance or full intensity in each of the red 550, green 600, and blue 650 channels) in the RGB color space. Note that the RGB properties corresponding to 0% transmittance and 100% transmittance may readily determined for a particular system and, accordingly, typically comprise known values. It has also been found that the same analysis performed for further histological samples 500 stained with the same dye reveals a reproducible spectral pattern, more particularly the characteristic path 940, for that dye in the RGB color space (see, for example, FIG. 4A for NFR and FIG. 4B for BCIP-NBT). Thus, a spectral pattern for the respective dye may be stored in a correspondence table, also referred to herein as a look-up table (LUT), describing the RGB properties of a dye from 0 to 100% transmittance in the RGB color space.

A typical correspondence table for a dye in an 8 bit image acquisition system may be defined with, for example, 256 rows and 4 columns, wherein each row 900 represents an intensity or transmittance increment. Three of the columns 905, 910, 915 represent each of the red 550, green 600, and blue 650 channels, while the fourth column 920 provides for indexing, as described further below. Each RGB triplet for the corresponding pixel in the image 450 is then entered in the correspondence table and indexed according to the minimum intensity or transmittance value of the triplet, the minimum intensity corresponding to the most absorbing (least intensity or transmittance) channel for the particular dye. Further, for each RGB triplet added to the correspondence table in the appropriate indexed row 900, the intensity values of the RGB triplet in the red 550, green 600, and blue 650 channels are added to the respective intensity values for any RGB triplet already inserted into the indexed row 900. In addition, for every RGB triplet added to an indexed row 900, the index in the fourth column 920 of the correspondence table is incremented by one so as to track the number of pixels defined by the same indexed row 900 in the correspondence table. This process is shown in, for example, FIGS. 2A–2C and may be, for instance, applied to a large set of images for each dye so as to provide an extensive and accurate spectral characterization of that dye. Thus, once all of the pixels in the set of images for that dye have been evaluated and inserted into the correspondence table according to the corresponding RGB triplet for respective pixel, the correspondence table is finalized. Thereafter, as shown in FIG. 3, the finalized correspondence table is normalized, wherein, for each indexed row 900, the summed intensity value in each of the red 550, green 600, and blue 650 channels is divided by the number of RGB triplets collected in that row, as indicated by the index value in the fourth column 920 of the correspondence table. Thus, the normalized RGB triplets 925, 930, 935 in the correspondence table comprise a representative line 945 through the RGB color space for the particular dye (see, for example, FIG. 4A for NFR and FIG. 4B for BCIP-NBT), wherein the representative line 945 extends along the previously determined characteristic path 940 for that dye.

Once normalized, the indexed rows will generally include normalized RGB triplets for the respective row. However, in some instances, some of the indexed rows may be missing an RGB triplet since, for example, an indexed row in the correspondence table may not necessarily be represented by a corresponding pixel in the image. That is, there may be instances where no RGB triplet for a pixel in the image meets the criteria for being added to a particular row. Further, in some instances, a significance criteria may be established so as to eliminate artifacts due to under-representation in the image. For example, an indexed row in the correspondence table may only be considered significant if 1000 or more pixels of the image have been indexed in that row. If an indexed row fails to meet the significance criteria, then any values in the three R, G, and B columns may be discarded or otherwise removed from the model for that dye. Accordingly, in instances where an indexed row of the normalized correspondence table does not include a normalized RGB triplet, an interpolation may be used to determine an approximated RGB triplet for any row lacking a normalized RGB triplet. Typically, the number of contiguous missing or insignificant RGB triplets is small and thus, for example, a cubic spline interpolation (see e.g., Numerical Recipes in C: The Art of Scientific Computing (ISBN 0-521-43108-5), pp. 113–117, Copyright (c) 1988–1992 by Cambridge University Press. Programs Copyright (c) 1988–1992 by Numerical Recipes Software) may be implemented so as to obtain an approximated RGB triplet for an empty row from both a known normalized RGB triplet at higher transmittance indexed row and a known normalized RGB triplet at a lower transmittance indexed row. However, one skilled in the art that other forms of interpolation may be equally applicable and effective depending on the requirements of the particular application. For example, a linear interpolation may be used in some instances. Accordingly, once the correspondence table has been completed, the respective dye is sufficiently modeled and the model is capable of being used in further applications as detailed below.

According to one advantageous embodiment of the present invention, once individual dyes have been modeled according to the procedure described above, two or more of these models for individual dyes may be combined so as to correspond to the staining protocol used for a particular expression. Thus, for example, for a melastatin expression, individual models for the counterstain (NFR) and the melastatin marker (BCIP-NBT) may be combined so as to facilitate evaluation of an unknown histological sample stained according to this protocol. Generally, the respective correspondence table for each dye defines transmittance values ranging from black (0% transmittance) to white (100% transmittance) with linear incremental steps (1/256% in transmittance for an 8 bit/channel image acquisition device) therebetween. Thus, as previously described, the LUT for a single dye is the representative line 945 extending through the characteristic path 940 for that dye in the RGB color space, wherein the representative line 945 may be expressed in a one-dimensional (1D) scale summarizing the spatial distribution of the dye in the RGB color space from 0 to 100% transmittance (See, for example, FIG. 5A for NFR and FIG. 5B for BCIP-NBT).

For a staining protocol specifying a certain combination of dyes, a model of that protocol for that dye combination may be realized from the orthogonal addition of the LUTs for the respective dyes, as shown, for example, in FIG. 5C. Accordingly, such a model would be defined as having one dimension per dye. Generally, the addition of, for example, two dyes such as those used in a melastatin expression, may be accomplished using the Lambert-Beer law to generate the appropriate RGB triplets for the particular dye combination. Thus, according to a particularly advantageous aspect of the present invention, the system 100 is configured to analyze the sample in accordance with the Lambert-Beer law. The Lambert-Beer law generally describes a proportionality that can be observed between the concentration of molecules in a solution (the concentration of the "molecular species" or the "sample") and the light intensity measured through the solution, and is typically expressed as:

$$OD = \epsilon \cdot l \cdot C \quad (1)$$

where OD is the optical density of the solution, $\epsilon$ is a proportionality constant called the molar extinction or absorption coefficient, l is the thickness of the sample, and C is the concentration of the molecular species. The absorption coefficient $\epsilon$ is specific to the molecular species and is typically expressed in units of $1 \cdot mol^{-1} \cdot cm^{-1}$.

This proportionality relationship defined by the Lambert-Beer law has been verified under the several conditions including, for example, monochromatic light illuminating the sample, low molecular concentration within the sample, generally no fluorescence or light response heterogeneity (negligible fluorescence and diffusion) of the sample, and lack of chemical photosensitivity of the sample. Further, another requirement for an analysis according to the Lambert-Beer law includes, for instance, correct Koehler illumination of the sample under the microscope. Koehler illumination is available with many modem microscopes, providing an even illumination of the sample in the image plane and allowing for effective contrast control. Koehler illumination is critical for certain processes such as, for example, densitometry analysis. Correct Koehler illumination is typically provided by, for example, a two-stage illuminating system for the microscope in which the source is imaged in the aperture of the sub-stage condenser by an auxiliary condenser. The sub-stage condenser, in turn, forms an image of the auxiliary condenser on the object. An iris diaphragm may also be placed at each condenser, wherein the first iris controls the area of the object to be illuminated, and the second iris varies the numerical aperture of the illuminating beam.

The Lambert-Beer law has an additive property such that, if the sample comprises several light-absorbing molecular species, for example, $s_1$ and $s_2$, having respective concentrations $C_1$ and $C_2$, the OD of a sample of thickness l (where $l_1 = l_2 = l$ for the sample, as indicated in the solution hereinafter) can be expressed as:

$$OD = \epsilon_1 \cdot l_1 \cdot C_1 + \epsilon_2 \cdot l_2 \cdot C_2 \quad (2)$$

This situation may occur, for example, in a biological analysis where a "scene," a field of view, or a portion of the sample has been stained with two dyes consisting of a marker dye for targeting the molecular species of interest and a counterstain for staining the remainder of the sample.

Once the microscope 150 has been configured to provide Koehler illumination for image acquisition and chromatic aberrations have been addressed, the additive property of the Lambert-Beer law can be applied to chromagen separation. For instance, the additive property of the Lambert-Beer law can be expanded to a situation in which the scene is analyzed in a color environment, generated by, for example, an RGB camera, separated into a red, green, and blue channel. In such an instance, the marker dye (or "dye 1") exhibits absorption coefficients, $\epsilon_{1r}$, $\epsilon_{1g}$, and $\epsilon_{1b}$, in the red, green and blue channels, respectively. Note that, in some instances, the analysis of the image in each of the red, green, and blue channels is equivalent to analyzing a red representation of the image across the red spectra, a green representation of the image across the green spectra, and a blue representation of the image across the blue spectra. Accordingly, the counterstain (or "dye 2") exhibits absorption coefficients, $\epsilon_{2r}$, $\epsilon_{2g}$, and $\epsilon_{2b}$, in the red, green and blue channels, respectively. Therefore, according to the additive property of the Lambert-Beer law, analysis of the sample in the RGB environment leads to three equations for the optical density thereof:

$$OD_r = \epsilon_{1r} \cdot l_1 \cdot C_1 + \epsilon_{2r} \cdot l_2 \cdot C_2 \quad (3)$$

$$OD_g = \epsilon_{1g} \cdot l_1 \cdot C_1 + \epsilon_{2g} \cdot l_2 \cdot C_2 \quad (4)$$

$$OD_b = \epsilon_{1b} \cdot l_1 \cdot C_1 + \epsilon_{2b} \cdot l_2 \cdot C_2 \quad (5)$$

where $OD_r$, $OD_g$, and $OD_b$ represent the optical densities of the sample measured in the red, green and blue channels, respectively. Still further, in the case of increased sample preparation complexity such as, for example, the treatment of the sample with three different dyes, equations (3), (4), and (5) become:

$$OD_r = \epsilon_{1r} \cdot l_1 \cdot C_1 + \epsilon_{2r} \cdot l_2 \cdot C_2 + \epsilon_{3r} \cdot l_3 \cdot C_3 \quad (6)$$

$$OD_g = \epsilon_{1g} \cdot l_1 \cdot C_1 + \epsilon_{2g} \cdot l_2 \cdot C_2 + \epsilon_{3g} \cdot l_3 \cdot C_3 \quad (7)$$

$$OD_b = \epsilon_{1b} \cdot l_1 \cdot C_1 + \epsilon_{2b} \cdot l_2 \cdot C_2 + \epsilon_{3b} \cdot l_3 \cdot C_3 \quad (8)$$

In such a situation, the three dyes may comprise, for instance, one marker dye and two counterstains, or two marker dyes and one counterstain, or even three separate marker dyes. For example, in continuance of the Melastatin™ expression application, the three dyes comprise the counterstain (Nuclear Fast Red), the marker (BCIP/NBT) and the natural pigment (melanin) of the histological sample. It will be understood by one skilled in the art, however, that this demonstrated property of the Lambert-Beer law may be expanded to included an even greater plurality of dye combinations in accordance with the spirit and scope of the present invention. Also note that, in some instances, one or more of the dyes may be initially excluded from the described analysis and then later characterized and added to the model for the combination of dyes, where necessary. For example, some samples may be characterized as having few or localized cells which express melanin. Accordingly, for many images of that sample, a model consisting only of the counterstain (Nuclear Fast Red) and the marker (BCIP/NBT) may be sufficient to analyze those images. However, where cells expressing melanin are present, the two-dye model may be supplemented with a third dye component corresponding to melanin, the third dye component being obtained and incorporated into the model as described herein. The sufficiency of the particular model and instances requiring the incorporation of additional dye components are further discussed below with respect to the concept of determining an error between respective pixels of the image of the sample and the applicable dye model.

One particularly advantageous aspect of the present invention utilizes a fast capture color imaging device such as, for example, a 3CCD RGB camera, for multi-spectral imaging of the markers over three distinct (red, green, and blue) channels so as to facilitate multi-spectral imaging of biological markers. Accordingly, the application of the Lambert-Beer law to a digital microscopy system 100 of the present invention recognizes that the Lambert-Beer law can also be expressed as:

$$OD_{(x,y)} = \log I_{0(x,y)} - \log I_{(x,y)} \quad (9)$$

for a digital image 450 of the sample 500 comprising a plurality of pixels arranged, for example, according to a Cartesian coordinate system, where (x,y) signifies a particular pixel in the image 450, $OD_{(x,y)}$ is the optical density of the sample 500 at that pixel, $I_{(x,y)}$ is the measured light intensity or transmittance of the sample 500 at that pixel, and $I_{0(x,y)}$ is the light intensity of the light source 200 as measured without any intermediate light-absorbing object, such as the sample. It will further be appreciated by one skilled in the art that the logarithmic relationship described in equation (9) may be expressed in various bases within the spirit and scope of the present invention. For example, the relationship may be expressed in base 2, base 10, or natural logarithms, wherein the various bases are related by respective proportionality constants (for example, $\ln(x)$ or $\log_e(x) = 2.3026 \log_{10}(x)$). Thus, the proportionality constant may be appropriately considered where relative comparisons are drawn in light intensities. Further, in quantitative microscopy according to the Lambert-Beer law, the proportionality relationship between the optical density OD of the sample and the dye concentrations is conserved. Therefore, for a prepared sample 500 examined by the system 100, the appropriate relation is expressed as:

$$ln\ I_0 - ln\ I = ln\ I_0/I = OD = \epsilon \cdot l \cdot C \quad (10)$$

Where, for example, an 8 bit RGB camera 300 is used in the system 100, the light intensity transmitted through the sample in each channel may be expressed as $2^8 (=256)$ values between 0 and 255. For example, the initial intensity $I_0$ of the light source 200, which corresponds to 100% transmittance, will preferably be expressed in each of the red 550, green 600, and blue 650 channels as a value approaching 255, representing the brightest possible value in each channel. The camera 300 and/or the light source 200 may be adjusted accordingly such that, in the absence of the sample, a pure "white" light will have an intensity value of 255 in each of the red 550, green 600, and blue 650 channels, corresponding to 100% transmittance. Conversely, in the absence of light, generally corresponding to transmittance approaching 0%, a "black image" will have an intensity value approaching 0 in each of the red 550, green 600, and blue 650 channels. At any pixel, the initial intensity $I_0$ of the light source 200, corresponding to 100% transmittance, is therefore expressed as the difference between the intensity value measured in presence of the light source 200 minus the intensity value measured in absence of the light source 200 for each of the red 550, green 600, and blue 650 channels. Because the intensity of the light source 200 may vary spatially across the image 450, or over the measured field of view, and because the magnifying objective 250 or other optical components may heterogeneously absorb light, 100% transmittance may be represented by various differential intensities over the measured field of view. However, since the optical density OD of the sample is expressed as the logarithm of the ratio of light transmittance in absence of the sample (initial intensity $I_0$) to light transmittance in presence of the sample (I), the optical density OD is largely spatially insensitive to small variations in the differential intensities over the measured field of view. Since the light source 200 remains substantially constant over time, or can be easily re-evaluated, the measurement of the light intensity for any pixel, in the presence of the sample, can be translated into the transmittance I at that pixel and in each of the red 550, green 600, and blue 650 channels. Once values for the initial intensity $I_0$ and transmittance I are determined, the optical density OD can be computed.

In the case of a protocol including two dyes such as, for example, the melastatin expression, the model for the combination of the two dyes is a 2D map corresponding to the orthogonal addition of the LUT for one dye with the LUT for the second dye, each LUT being expressed as a one-dimensional (1D) scale (FIGS. 5A and 5B) describing the representative line 945 extending through the characteristic path 940 for that dye in the RGB color space from 0 to 100% transmittance. Each pixel at an (x,y) location on the 2D map (FIG. 5C) thus corresponds to the addition of dye 1 (i.e. NFR) and dye 2 (i.e. BCIP-NBT). That is, each pixel at an (x,y) location on the 2D map corresponds to the combination of an RGB triplet from the LUT of dye 1 at indexed row x with an RGB triplet from the LUT of dye 2 at indexed row y. Accordingly, the resulting RGB triplet for the pixel at (x,y) in the 2D map may be expressed as:

$$R_{(x,y)} = 255/exp(OD_{R(x,y)}) \quad (11)$$

$$G_{(x,y)} = 255/exp(OD_{G(x,y)}) \quad (12)$$

$$B_{(x,y)} = 255/exp(OD_{B(x,y)}) \quad (13)$$

where $R_{(x,y)}$, $G_{(x,y)}$, and $B_{(x,y)}$ are transmittances in each of the red 550, green 600, and blue 650 channels, respectively. However, though transmittances generally do not exhibit an additive property, optical densities do exhibit an additive property. Accordingly, for an 8 bit/channel system, the optical densities in each of the red 550, green 600, and blue 650 channels for the pixel at (x,y) in the 2D map may be expressed as:

$$OD_{R(x,y)} = OD_{Rx} + OD_{Ry} = Ln(255/R_x) + Ln(255/R_y) \quad (14)$$

$$OD_{G(x,y)} = OD_{Gx} + OD_{Gy} = Ln(255/G_x) + Ln(255/G_y) \quad (15)$$

$$OD_{B(x,y)} = OD_{Bx} + OD_{By} = Ln(255/B_x) + Ln(255/B_y) \quad (16)$$

As such, because every pixel in the 2D model is defined by an RGB triplet determined from the combination of an appropriate RGB triplet for each of the two dyes, the 1D model of each dye, as well as the 2D model of combination of the two dyes, may be separately displayed in a 3D RGB color space, as shown in FIG. 4C.

After the model for the combination of dyes used for the particular protocol has been completed, the model may then be applied to unknown histological samples stained according to that protocol. Accordingly, the system 100 is then used to capture an image 450 of an unknown histological sample 500 stained according to a protocol, such as the melastatin expression, for which an appropriate model has been previously developed. As with the dye modeling procedure, the image 450 of the unknown histological sample 500 is analyzed on a per pixel basis. Thus, each pixel $P_i$ in the image 450 of the unknown histological sample 500 is defined by an RGB triplet ($R_i$, $G_i$, $B_i$) and one particularly advantageous aspect of the present invention recognizes that such a pixel $P_i$ can be correlated with a color $P_m$, defined by an RGB triplet ($R_m$, $G_m$, $B_m$), in the model. The color $P_m$ corresponds to the dye combination which minimizes the Euclidean distance between the pixel $P_i$ and the model in the RGB color space, as shown in FIG. 6. $P_m$ is thereby determined by minimizing the solution of $d(P_i, P_m)$ over the model, wherein:

$$d(P_i, P_m) = SQRT((R_i - R_m)^2 + (G_i - G_m)^2 + (B_i - B_m)^2) \quad (17)$$

Further, the minimized Euclidean distance between $P_i$ and $P_m$ corresponds to an error between the real image and the model and thus indicates the efficiency of the model in describing the real image. Such a concept can be graphically displayed in the RGB color space and may be used to evaluate the sample, as shown, for example, in FIG. 7. More particularly, the mean error of the pixels representing a specific object (i.e. the mask of a nucleus) within the image can be used to either accept or reject the model for that specific object. According to this procedure, objects within the image may be identified as including dyes other than the dyes used to construct the model. For example, in the melastatin expression example, a significant mean error in a portion of the image of the sample may indicate that the structure being studied in the image comprises the natural pigment (melanin) which was not considered in developing the model of the two other dyes, contamination, or an unidentified artifact. In contrast, a small or nonexistent error my indicate that the portion of the sample being studied includes tissue which is stained by any or all of the dyes used to develop the model for that protocol. Further, for instance, a significant constant error found across all of the pixels in the image of the unknown histological sample may indicate that the model for the protocol has shifted compared to the unknown histological sample. In still other instances, significant error across all of the pixels of the image may indicate that one or more improper dyes have been used to stain the unknown histological sample.

In instances where the source of a significant mean error is identifiable, for example, from an examination of the image, the dye model may be supplemented with the addition of a further dye component so as to provide an improved model for analyzing the image or an object within the image. For instance, some images may include cells expressing melanin, which may be identified as such by one skilled in the art viewing those images. Such an image is shown, for example, in FIG. 13A, wherein the melanin component is indicated by the brownish component of the image. Accordingly, for a dye model comprising the counterstain (Nuclear Fast Red) and the marker (BCIP/NBT), an error distribution, such as shown in FIG. 13B, indicates the melanin component in red, whereas the blue component indicates areas of the image sufficiently described by the two dye model so as to exhibit little or no error for those pixels. In such instances, a separate melanin source or sample may be characterized as detailed herein and the results then added to existing dye model. That is, for example, the Melastatin™ expression described herein may be analyzed by a three dye model comprising a component for the counterstain (Nuclear Fast Red), a component for the marker (BCIP/NBT), and a component for the natural pigment (melanin) where an image of the stained histological sample exhibits cells expressing melanin. FIG. 13C illustrates an error distribution analysis of the image shown in FIG. 13A with the melanin component added to the two dye model so as to produce a three dye model, the predominantly blue error image indicating that the three dye model is now sufficient to describe all of the pixels in the image. Note also that one skilled in the art will appreciate that adding the additional dye component to the dye model may be readily accomplished as detailed herein.

Once an error has been determined for each pixel of the image, further analysis of these errors may provide other useful information with respect to the image. For example, for as given object, such as a cell, within the image, the errors for the pixels comprising the object may be integrated to provide an indication of whether the object is stained with the dyes comprising the model so as to evaluate whether that object is valid for further assessment. In some instances, the evaluated image may be configured so as to provide for verification of the particular dye model, as will be appreciated by one skilled in the art. Further, an analysis of the errors may be structured so as to, for example, provide for detection of objects within an image that are not described by the particular dye model, indicate variations in the preparation of multiple samples, and variations within a single sample. Thus, the evaluation of error between the image and the model may advantageously provide significant and valuable information for evaluation of the sample as described herein.

Once the pixels of the image of the unknown histological sample have been captured and evaluated by the system 100, the pixels may be evaluated according to the respective corresponding color $P_m$ to determine the appropriate RGB triplet contributed by each dye in the 2D combination model (i.e. ($R_{BCIP}$, $G_{BCIP}$, $B_{BCIP}$) and ($R_{NFR}$, $G_{NFR}$, $B_{NFR}$)) from the LUT of the respective dye, as previously described and as shown, for example, in FIG. 8. As such, the image of the unknown histological sample may then be displayed as the captured image and as individual images each representing the distribution of a respective dye. As previously described, each dye has a concentration represented by a transmittance ranging from 0% to 100% transmittance, the transmittance range being further represented by gray values of 0 to 255 for an 8 bit/channel system. As such, since the 2D combination model is used to evaluate the image of the unknown histological sample, whenever a pixel color $P_m$ (RGB triplet) in the image of the unknown sample is not present in the dye combination model, as manifested in the calculation of an error greater than zero, the proposed solution must be verified with respect to the theory of optical densities and the Lambert-Beer Law. That is, when an RGB value for a pixel in the image of the unknown histological sample does not correspond to the dye combination model, that RGB value may include some noise from, for example, the histological sample, the camera, the optical systems, or other noise source. In addition, or in the alternative, the errant RGB value for the pixel may indicate that the RGB value was generated from a different dye combination as compared to the dye combination model.

Accordingly, in order to ensure robustness and adequacy of the dye combination model, one advantageous aspect of the present invention utilizes a particular approach, as shown in FIG. 9. First, the dye combination model space investigated during the search for the optimal dye combination is restricted to a bounded region 950 with respect to the investigated pixel of the image of the unknown histological sample. More particularly, the bounded region 950 in which to determine the optimal dye combination for the investigated pixel is defined by the LUT indexed row 955, 960 for each individual dye that separates RGB values having equal or higher transmittance with respect to the investigated pixel from RGB values having a lower transmittance lower with respect to the investigated pixel in any of the red 550, green 600, and blue 650 channels. That is, the LUT indexed row defining the bounded region 950 for the respective dye cannot have a transmittance in any of the red 550, green 600, and blue 650 channels that is lower than the transmittance in the corresponding channel of the investigated pixel. The bounded region 950 is thus defined on the premise that the search for the optimal dye combination cannot be conducted among dye concentrations, for any dye and in any of the red 550, green 600, and blue 650 channels, that would individually exhibit a higher optical density than the investigated pixel. As such, the bounded region 950 may also be indicated on an error map in the RGB color space, as shown in FIG. 10, illustrating, for any pixel, the distance of the investigated pixel to the dye combination model. Solving for the optimal dye combination for each pixel of the image of the unknown histological sample therefore facilitates, for example, visualization and quantification of the amount of each dye (counterstain, marker or natural pigment) distributed over the image. For example, the image of the sample, as shown in FIG. 11A, may be shown as an artificial image of only one of the component dyes (FIG. 11B for NFR only and FIG. 11C for BCIP-NBT only). Such artificial images for each of the component dyes are typically reconstructed on a per pixel basis from the LUT for each respective dye. That is, the artificial image for that single dye component is constructed on a per pixel basis from the actual transmittance value in each of the red, green, and blue channels of the appropriate index row of the LUT for that dye, wherein the appropriate index row for the respective pixel corresponds to the contribution of that dye as determined from the optimal dye combination for that pixel. Alternatively, the original image (FIG. 11A) may be shown as an artificial gray level image of only one of the component dyes (FIG. 11D for NFR only and FIG. 11E for BCIP-NBT only). Such gray level artificial images are also typically reconstructed on a per pixel basis from the LUT for each respective dye. However, in these instances, the gray level artificial image for the single dye component is constructed on a per pixel basis from the appropriate index row of the LUT for that dye, wherein the appropriate index row for the respective pixel corresponds to the contribution of that dye as determined from the optimal dye combination for that pixel. More particularly, as previously described, the index row represents the RGB channel with the least transmittance which, when combined with the initial intensity $I_0$, allows the particular pixel to be expressed in terms of an optical density OD with the gray level artificial image being constructed accordingly, as will be appreciated by one skilled in the art. One skilled in the art will also appreciate that, for example, subsequent quantification of each dye component within the image, or other qualitative or quantitative analysis of an image, may be further undertaken once the artificial images have been determined using various forms of image processing or other techniques commonly used in image analysis and such subsequent analysis, though not described in detail herein for the sake of brevity, will be considered to be within the scope of the embodiments of the invention as presented herein.

As previously discussed, though embodiments of the present invention are described herein, for the sake of example, in terms of a video-microscopy system, it will be understood and appreciated by one skilled in the art that the concepts describe herein may have a broad applicability to non-microscopy systems. For instance, the concepts described herein may be applicable where one or more color components may be separately characterized such that useful information may be gleaned from the distribution of such color components with respect to an unknown sample comprising the color components. Such instances may be present where, for example, one or more known liquid may be characterized, as disclosed herein, and those characterizations then applied to the determination of the characteristics of an unknown liquid solution comprised of the individual known liquids, such liquids comprising, for example, paints or stains. In a more general sense, the concepts described herein may be applicable where digital image characterization of individual components may be used to analyze an image of an unknown sample, which may not necessarily be comprised of the known individual components, wherein much information may be obtained from a comparison of the unknown sample to the selected model, as will be appreciated by one skilled in the art.

Further advantageous aspects of the present invention are realized as a result of the dye identification techniques using color video imaging as previously described herein. For example, an artificial image of the field of view may be generated in an RGB color space or in gray levels as a substantially real time or live image, or as a still image, for combinations of the dyes comprising a marker and/or a counterstain used for the staining protocol for the sample. More particularly, an artificial image of the field of view may be produced which shows the sample as affected by all of the dyes, the sample as affected by one or more marker dyes, or the sample as affected by the counterstain. Consequently, since the dyes used to prepare the sample are characterized by the system, the capabilities of the system may be extended such that, for instance, the sample or field of view may be automatically scanned to detect a specific region of interest as identified by the characteristics of a particular dye (or lack of those characteristics) or to affect or facilitate a task to be performed on that specific region of interest.

According to one embodiment of the present invention, the system may be configured so as to be capable of detecting one or more particular dyes which have been previously characterized by the system. In some instances, such a dye may comprise, for example, the ink from a particular pen or similar ink marker that has been characterized by the system as having unique color features, these unique color features being retained by the system as a corresponding LUT for that dye. It follows that the system may be configured to recognize and respond to portions of the field of view in which this dye is identified and that, in some instances, the one or more particular markers may comprise a tangible portion of such a system as described herein. For instance, such a pen may be used, for example, where an operator such a pathologist or a cytotechnologist identifies special areas of interest on a sample-containing glass or plastic slide. A special area of interest may comprise, for example, a potential diagnostic area or a reference area. The operator, using the pen, may then surround the area with a line of ink from that pen. After processing a number of slides, the operator may feed the slides into, for instance, an automatic scanning system for quantitative evaluation. Having been configured to detect the ink from the pen, the system may then inclusively identify the area of interest, corresponding to the area within the ink line, circled by the operator with the pen. The system may thereafter appropriately process that area of the slide where, for example, one color of pen ink may indicate that a particular diagnostic evaluation must be performed, while another color of ink may indicate that the area contains a calibration or reference material and would call for the system to run a corresponding calibration procedure. Note that, in addition to slides, the described technique may be readily adapted to examine other mounting forms for microscopic material such as, for example, microtiter plates or microarrays. Thus, it will be appreciated by one skilled in the art that the capabilities of such embodiments of the system, configured to recognize particular dyes or inks, may extend to many different automatic scanning processes where interactive marking of areas of interest with specific pens, the pens having different color inks previously evaluated by the system, may be used to automatically designate and actuate a subsequent evaluation or other processing of that area of interest by an appropriate component of the system or other specified device.

Additionally, the artificial images of the field of view may also facilitate the presentation of the data in a configuration allowing identification and selection of meaningful objects or areas of interest as, for example, still images in a report prepared for diagnostic or other reporting purposes. Still further, the artificial image of the field of view may also be used to facilitate the identification and extraction of selected features of the treated sample. For example, marked point processes, contextual analysis, and/or geo-statistics may be used to identify and extract features from the image based on, for instance, a spatial distribution analysis of a particular dye. Such a feature extraction capability would also allow, for example, fields of view or objects of interest to be sorted, flagged, or otherwise identified or grouped based on, for instance, the overall content of a given marker dye or a selected ratio of particular marker. Where, for example, a threshold criteria can be established, such a capability would be the detection of rare, worsening, or other serious events. Proceeding further, classifiers based specifically on the image processing resulting from the counterstain and/or marker dye specific images may then be established and used to evaluate the presence of certain cell types or to perform a diagnosis based upon the field of view. Such classifiers may usually also encompass other informative features such as, for example, detail based upon the morphology or the texture of the cells.

Still further, another advantageous aspect of the present invention is realized where the system is capable of processing the image data at a faster rate than the images are acquired. The enhanced speed at which the image data is processed may allow, for example, features indicated by a particular marker dye to be processed and classified. Accordingly, various conditions may be identified based upon predetermined criteria. As such, visual and/or sonic alarms may be established and/or mapped in conjunction with the processing of the image data. Thus, in some instances, the operator's attention may be directed to a specific field of view or object of interest when a characteristic of a marker attains a predetermined level in, for example, intensity or presence in a particular field.

FIG. 12 is a schematic representation of a practical realization of an extended system configuration according to one embodiment of the present invention. In such an implementation, the system 100 or workstation is centered about a microscope 150. The microscope 150 may include one or more robotic components including, for example, a motorized stage, an automatic focus mechanism, a motorized objective changer, and an automatic light intensity adjustment. The system 100 may also include various input devices such as, for instances, cameras 300a and 300b having fast automatic focusing and configured for acquiring low-resolution and high-resolution images, a flat bed linear scanners 310 used for acquiring low-resolution images, a grossing station 320, and a voice-recording device 330, which are all linked to a computer device 350 through various data transmission links 400. The workstation 100 can be part of a Local Area Network (LAN) 700, but may also be configured to support different communication protocols such that available communication channels such as, for example, a standard telephone line, an ISDN connection, or a T1 line, can readily connect the workstation 100 to other components or devices over large distances via a Wide Area Network (WAN) 750 as will be appreciated by one skilled in the art.

If the pathology workstation 100 is configured to operate in an integrated environment, the WAN 700 or LAN 750 connection may permit access to, for instance, existing reference databases 800 and Hospital Information Systems (HIS) 850. With such a configuration, new samples and/or cases may readily be compared with the pictures and accompanying information of previously-accumulated reference cases. Further, images acquired from the samples and/or slides being examined at the workstation 100 can be complemented with the patient and case history as necessary.

In the extended configuration embodiment as shown in FIG. 12, the pathology workstation 100 is particularly configured for a comprehensive sample evaluation. For example, with information and digital pictures of the initial gross biological sample, images of the slides prepared from the sample can be prepared and processed as described herein. The patient and case information, the images, and the resulting quantitative information about the cell components of the sample and the sample architecture (in the case of, for instance, tissue samples) can also be collected, integrated if necessary, and stored in a single database. If, for example, an initial or second expert opinion is needed or if the slide is used for training or proficiency testing, the communication capabilities of the extended configuration along with the automation features of the microscope 150 may allow the workstation 100 to be used as a tele-pathology system. For example, high-resolution images directed to features or objects of interest characterizing a questionable situation on a particular slide may be electronically forwarded to the expert and/or to the audited candidate. In some instances, an overview picture of the slide may be provided, wherein the automated microscope 150 is used to scan the slide automatically on, for example, a field by field basis. The corresponding digital images may then be stored in the memory of the computer device 350. Where a field by field basis is used, the edges of adjacent fields may be precisely matched using correlation algorithms, so as to provide a single large overview image of the entire slide. Such an overview image may assist the reference pathologist in making an assessment of the information. In some instances, the reference pathologist may remotely control the workstation 100 from a remote site to acquire necessary and/or supplemental images which may be required so as to provide a correct and thorough assessment of the slide.

Subsequently, the information accumulated by the workstation 100 for a studied case such as, for instance, real or mathematically generated images, measurement results and graphical representations thereof, patient data, preparation data, and screening maps, may be selectively integrated into a report which can either be printed or accessed electronically. Such a report would provide a comprehensive picture of the case under evaluation and would also facilitate quality assurance and standardization issues.

It will be understood that the methodology and procedures detailed herein in conjunction with the system 100 specify a method of quantifying an amount of a molecular species from an image of a sample captured by an RGB camera in a video-microscopy system. One skilled in the art will also appreciate that such a method may be automated so as to provide a computer software program product, executable on a computer device, having executable portions capable of quantifying the amount of a molecular species from a digital image of a sample captured by a color image acquisition device, such as an RGB camera, in a video-microscopy system. Accordingly, embodiments of the system 100 describe the implementation of the method and/or the corresponding computer software program product which may be accomplished in appropriately configured hardware, software, or a combination of hardware and software in accordance with the spirit and scope of the present invention.

Thus, embodiments of the present invention comprise a colorimetric analysis technique for prepared samples that provides effective detection and quantification of species of interest that overcomes limiting factors of prior art techniques such as, for example, spectral overlapping, mixing of colors due to spatial overlap of membrane and nuclear markers, limited spectral resolution of the acquisition device, calibration particularities, the subjectivity of the detection and quantification process, and inconsistencies between human operators of the analysis equipment. Embodiments of the present invention further provide an image processing technique which does not rely upon the subjective detection of contrast within the prepared sample or a complex and voluminous analysis of the sample at specific wavelengths of light using a combination of light sources and filters. Therefore, embodiments of the present invention provide a simpler and more effective colorimetric analysis technique that overcomes detection and quantification limitations in prior art analysis techniques, reduces subjectivity and inconsistency in the sample analysis, and is capable of providing the necessary analysis information about the sample, once an image of the sample is captured, without relying upon further examination of the sample to complete the analysis.

More particularly and as demonstrated, the analysis (detection and quantification of a molecular species of interest) of the prepared sample is accomplished through the measurement of light intensities that are manifested in a digital image of the sample captured by a color image acquisition device. Since the analysis is relatively image-dependent, rather than sample-dependent, redundant images may be captured for analysis, while many samples may be processed so as to capture the necessary images within a relatively short period of time. Once the image data has been captured and stored, the actual analysis may occur at a later time or as needed without requiring the physical presence of the actual sample. Such an analysis may be further applied to examining the entire sample or even the entire slide. Thus, embodiments of the present invention provide an expeditious quantitative video-microscopy system that permits the use of such a system as a routine or "production" tool capable of accomplishing a relatively high analysis throughput. As such, significant advantages are realized by embodiments of the present invention as compared to prior art quantitative microscopy systems which were typically limited in sample throughput and analysis, thus generally making such systems more useful as research tools.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of modeling a dye, said method comprising:
   determining a transmittance of the sample treated with the dye from a color image of the treated sample, the image comprising a plurality of pixels, in each of a red, green, and blue channel of an RGB color space and for each pixel of the image so as to form am RGB triplet for each pixel;
   grouping the RGB triplets according to the minimum transmittance in the red, green, and blue channels for the respective RGB triplet;
   normalizing each group RGB triplets by summing the transmittances in each of the respective red, green, and blue channels and then dividing each of the summed transmittances by the number RGB triplets in the respective group so as to form respective normalized RGB triplets; and
   tabulating the normalized RGB triplets according to the minimum transmittance of each normalized RGB triplet so as to form a correspondence table for the dye, the correspondence table extending in transmittance increments between 0% and 100% transmittance.

2. A method according to claim 1 further comprising capturing an image of the treated sample with a color image acquisition device so as to form the color image of the treated sample.

3. A method according to claim 1 further comprising determining, when a transmittance increment in the correspondence table is without a normalized RGB triplet, an approximated transmittance in each of the red, green, and blue channels so as to form an approximated normalized RGB triplet for that transmittance increment.

4. A method according to claim 3 wherein determining the approximated normalized RGB triplet further comprises determining a reference transmittance increment having a normalized RGB triplet, both at a higher transmittance increment and a lower transmittance increment in the correspondence table, with respect to the transmittance increment without the normalized RGB triplet, and then interpolating between the respective transmittances in each of the red, green, and blue channels of the reference transmittance increments so as to form an approximated normalized RGB triplet for the transmittance increment without the normalized RGB triplet.

5. A method according to claim 1 farther comprising establishing a significance threshold for the number of RGB triplets in a group and, for any group failing to meet the significance threshold, discarding the RGB triplets therein as being insignificant.

6. A method according to claim 1 further comprising plotting the RGB triplets for the pixels of the image in an RGB color space so as to obtain a three-dimensional RGB representation of the respective dye, prior to normalizing each group of RGB triplets.

7. A method according to claim 1 further comprising plotting the normalized RGB triplets in an RGB color space so as to obtain a characteristic RGB path of the respective dye through the RGB color space.

8. A method according to claim 1 further comprising plotting the normalized RGB triplets on a one-dimensional scale so as to graphically represent the correspondence table.

9. A method according to claim 2 wherein capturing an image of the treated sample further comprises capturing an image of the sample in a video microscopy system with at least one of an RGB camera and an RGB-configured scanner.

10. A method according to claim 2 wherein capturing an image of the treated sample further comprises illuminating the sample under Koehler illumination conditions.

11. A method according to claim 2 wherein capturing an image of the treated sample further comprises capturing an image of the sample in a chromatic aberration-corrected video-microscopy system.

12. A method according to claim 2 wherein capturing an image of the treated sample further comprises illuminating the sample with a light source and determining a transmitted intensity of the light transmitted therethrough in each of the red, green, and blue channels.

13. A method of modeling a combination of a plurality of dyes, said method comprising:

forming a corresponding table for each of the plurality of dyes, comprising; determining a transmittance of a sample treated with the respective dye from a color image of the treated sample, the image comprising a plurality of pixels, in each of a red, green, and blue channel of an RGB color space and for each pixel of the image so as to form an RGB triplet for each pixel;

grouping the RGB triplets according to the minimum transmittance in the red, green, and blue channels for the respective RGB triplet;

normalizing each group of RGB triplets by summing the transmittances in each of the respective red, green, and blue channels and then dividing each of the summed transmittances by the number of RGB triplets in the respective group so as to form respective normalized RGB triplets; and tabulating the normalized RGB triplets according to the minimum transmittance of each normalized RGB triplet so as to form the correspondence table for the respective dye, the correspondence table extending in transmittance increments between 0% and 100% transmittance; and orthogonally adding the correspondence tables of the plurality of dyes so as to form a dye space representation of the plurality of dyes, the dye space representation having one dimension for each dye and providing a reference model for a combination of the plurality of dyes.

14. A method according to claim 13 further comprising capturing an image of the treated sample with a color image acquisition device so as to form the color image of the treated sample.

15. A method according to claim 13 further comprising determining, when a transmittance increment in the correspondence table for a dye is without a normalized RGB triplet, an approximated transmittance in each of the red, green, and blue channels so as to form an approximated normalized RGB triplet for that transmittance increment.

16. A method according to claim 15 wherein determining the approximated normalized RGB triplet further comprises determining a reference transmittance increment having a normalized RGB triplet, both at a higher transmittance increment and a lower transmittance increment in the correspondence table for the dye, with respect to the transmittance increment without the normalized RGB triplet, and then interpolating between respective transmittances in each of the red, green, and blue channels of the reference transmittance increments so as to form an approximated normalized RGB triplet for the transmittance increment without the normalized RGB triplet.

17. A method according to claim 13 further comprising establishing a significance threshold for the number of RGB triplets in a group and, for any group failing to meet the significance threshold, discarding the RGB triplets therein as being insignificant.

18. A method according to claim 13 further comprising plotting the RGB triplets for the pixels of the image in an RGB color space so as to obtain a three-dimensional RGB representation of the respective dye, prior to normalizing each group of RGB triplets.

19. A method according to claim 13 further comprising plotting the RGB triplets for the pixels of the images for each of the plurality of dyes in an RGB color space so as to obtain a three-dimensional representation of a combination of the plurality of dyes, prior to normalizing each group of RGB triplets.

20. A method according to claim 13 further comprising plotting the normalized RGB triplets in an RGB color space so as to obtain a characteristic RGB path of the respective dye through the RGB colorspace.

21. A method according to claim 13 further comprising plotting the normalized RGB triplets on a one-dimensional scale so as to graphically represent the correspondence table.

22. A method according to claim 13 wherein orthogonally adding the correspondence tables of the plurality of dyes further comprises orthogonally adding the correspondence tables of the plurality of dyes according to the Lambert-Beer law.

23. A method according to claim 13 further comprising plotting the dye space representation of the plurality of dyes on a scale having a number of dimensions corresponding to the number of dyes.

24. A method according to claim, 13 wherein orthogonally adding the correspondence tables of the plurality of dyes further comprises orthogonally adding the correspondence tables of the plurality of dyes so as to form a resultant correspondence table for the combined plurality of dyes the resultant correspondence table comprising a plurality of resultant RGB triplets extending between 0% and 100% transmittance.

25. A method according to claim 14 wherein capturing an image of the treated sample further comprises capturing an image of the sample in a video microscopy system with at least one of an RGB camera and an RGB-configured scanner.

26. A method according to claim 14 wherein capturing an image of the treated sample further comprises illuminating the sample under Koehler illumination conditions.

27. A method according to claim 14 wherein capturing an image of the treated sample further comprises capturing an image of the sample in a chromatic aberration-corrected video-microscopy system.

28. A method according to claim 14 wherein capturing an image of the treated sample further comprises illuminating the sample with a light source and determining a transmitted intensity of the light transmitted therethrough in each of the red, green, and blue channels.

29. A system for modeling a dye indicative of a molecular species in a sample from an image of the sample treated with the dye, said system comprising:

a computer device comprising:

a processing portion configured to determine a transmittance of the sample treated with the dye from a color image of the treated sample, the image comprising a plurality of pixels, in each of a red, green, and blue channel of an RGB color space and for each pixel of the image so as to form an RGB triplet for each pixel;

a processing portion configured to group the RGB triplets according to the minimum transmittance in the red, green, and blue channels for the respective RGB triplet;

a processing portion configured to normalize each group of RGB triplets by summing the transmittances in each of the respective red, green, and blue channels and then dividing each of the summed transmittances by the number of RGB triplets in the respective group so as to form respective normalized RGB triplets; and a processing portion configured to tabulate the normalized RGB triplets according to the minimum transmittance of each normalized RGB triplet so as to form a correspondence table for the dye, the correspondence table extending in transmittance increments between 0% and 100% transmittance.

30. A system according to claim 29 further comprising a color image acquisition device operably engaged with the computer system and configured so as to be capable of capturing a magnified digital image of the sample, the image acquisition device comprising at least one of an RGB-configured scanner and a microscope operably engaged with an RGB camera.

31. A system according to claim 30 wherein the computer device further comprises a processing portion configured to direct the image acquisition device to capture the color image of the treated sample.

32. A system according to claim 29 wherein the computer device further comprises a processing portion configured to determine, when a transmittance increment in the correspondence table is without a normalized RGB triplet, an approximated transmittance in each of the red, green, and blue channels so as to form an approximated normalized RGB triplet for that transmittance increment.

33. A system according to claim 32 wherein the processing portion for determining the approximated normalized RGB triplet is further configured to determine a reference transmittance increment having a normalized RGB triplet, both at a higher transmittance increment and a lower transmittance increment in the correspondence table, with respect to the transmittance increment without the normalized RGB triplet, and then to interpolate between the respective transmittances in each of the red, green, and blue channels of the reference transmittance increments so as to form an approximated normalized RGB triplet for the transmittance increment without the normalized RGB triplet.

34. A system according to claim 29 wherein the processing portion for grouping the RGB triplets is further configured to apply a significance threshold for the number of RGB triplets in a group and, for any group failing to meet the significance threshold, to discard the RGB triplets therein as being insignificant.

35. A system according to claim 29 wherein the computer device further comprises a processing portion configured to plot the RGB triplets for the pixels of the image in an RGB color space so as to provide a three-dimensional RGB representation of the respective dye.

36. A system according to claim 29 wherein the computer device further comprises a processing portion configured to plot the normalized RGB triplets in an RGB color space so as to obtain a characteristic RGB path or the respective dye through the RGB color space.

37. A system according to claim 29 wherein the computer device further comprises a processing portion configured to plot the normalized RGB triplets on a one-dimensional scale so as to graphically represent the correspondence table.

38. A system according to claim 30 wherein the image acquisition device and the computer device are further configured to cooperate to form a chromatic aberration-corrected video-microscopy system.

39. A system according to claim 30 further comprising a light source configured to illuminate the sample, wherein the processing portion for determining a transmittance of the treated sample is further configured to direct a measurement of a transmitted intensity of light transmitted through the sample in each of the red, green, and blue channels.

40. A system according to claim 39 wherein the light source is further configured to illuminate the sample under Koehler illumination conditions.

41. A system for modeling a plurality of dyes from a corresponding plurality of samples using an image of each sample, each sample being treated with a different one of the plurality of dyes, said system comprising:
a computer device comprising:
a processing portion configured to form a correspondence table for each of the plurality of dyes from the image of the respective sample comprising;
determining a transmittance of the sample treated with the dye from a color image of the respective treated sample, the image comprising a plurality of pixels, in each of a red, green, and blue channel of an RGB color space and for each pixel of the image so ms to form an RGB triplet for each pixel;
grouping the RGB triplets according to the minimum transmittance in the red, green, and blue channels for the respective RGB triplet;
normalizing each group of RGB triplets by summing the transmittances in each of the respective red, green, and blue channels and then dividing each of the summed transmittances by the number of RGB triplets in the respective group so as to form respective normalized RGB triplets; and
tabulating the normalized RGB triplets according to the minimum transmittance of each normalized RGB triplet so as to form the correspondence table for the respective dye, the correspondence table extending in transmittance
increments between 0% and 100% transmittance; and
a processing portion configured to orthogonally add the correspondence tables of the plurality of dyes so as to form a dye space representation of the plurality of dyes, the dye space representation having one dimension for each dye and providing a reference model for a combination of the plurality of dyes.

42. A system according to claim 41 further comprising a color image acquisition device operably engaged with the computer device and configured so as to be capable of capturing a magnified digital image of each respective sample, the image acquisition device comprising at least one of an RGB-configured scanner and a microscope operably engaged with an RGB camera.

43. A system according to claim 42 wherein the computer device further comprises a processing portion configured to direct the image acquisition device to capture the color image of the respective treated sample.

44. A system according to claim 41 wherein the computer device further comprises a processing portion configured to determine, when a transmittance increment in the correspondence table is without a normalized RGB triplet, an approximated transmittance in each of the red, green, and blue channels so as to form, an approximated normalized RGB triplet for that transmittance increment.

45. A system according to claim 44 wherein the processing portion for determining the approximated normalized RGB triplet is further configured to determine a reference transmittance increment having a normalized RGB triplet, both at a higher transmittance increment and a lower transmittance increment in the correspondence table, with respect to the transmittance increment without the normalized RGB triplet, and then to interpolate between the respective transmittances in each of the red, green, and blue channels of the reference transmittance increments so as to form an approximated normalized RGB triplet for the transmittance increment without the normalized RGB triplet.

46. A system according to claim 41 wherein the processing portion for forming a correspondence table for each of the plurality of dyes is further configured to apply a significance threshold for the number of RGB triplets in a group and, for any group failing to meet the significance threshold, to discard the RGB triplets therein as being insignificant.

47. A system according to claim 41 wherein the computer device further comprises a processing portion configured to plot the RGB triplets for the pixels of the image in an RGB color space so as to provide a three-dimensional RGB representation of the respective dye.

48. A system according to claim 41 wherein the computer device further comprises a processing portion configured to plot the RGB triplets for the pixels of the images for each of the plurality of dyes in an RGB color space so as to obtain a three-dimensional representation of a combination of the plurality of dyes.

49. A system according to claim 41 wherein the computer device further comprises a processing portion configured to plot the normalized RGB triplets in an RGB color space so as to obtain a characteristic RGB path of the respective dye through the RGB color space.

50. A system according to claim 41 wherein the computer device further comprises a processing portion configured to plot the normalized RGB triplets on a one-dimensional scale so as to graphically represent the correspondence table.

51. A system according to claim 41 wherein the processing portion for orthogonally adding the correspondence tables of plurality of dyes is further configured to orthogonally add the correspondence tables of the plurality of dyes according to the Lambert-Beer law.

52. A system according to claim 41 wherein the computer device further comprises a processing portion configured to plot the dye space representation of the plurality of dyes on a scale having a number of dimensions corresponding to the number of dyes.

53. A system according to claim 41 wherein the processing portion for orthogonally adding the correspondence tables of the plurality of dyes is further configured to orthogonally add the correspondence tables of the plurality of dyes so as to form a resultant correspondence table for the combined plurality of dyes the resultant correspondence table comprising a plurality of resultant RGB triplets extending between 0% and 100% transmittance.

54. A system according to claim 42 wherein the image acquisition device and the computer device are further configured to cooperate to form a chromatic aberration-corrected video-microscopy system.

55. A system according to claim 41 wherein the processing portion for forming a correspondence table for each of the plurality of dyes is further configured to direct a measurement of a transmitted intensity of light transmitted through the sample in each of the red, green, and blue channels.

56. A system according to claim 41 wherein the computer device further comprises a processing portion configured to direct a light source to illuminate the sample under Koehler illumination conditions.

57. A computer-readable medium encoded with a computer program capable of modeling a dye, indicative of a molecular species in a sample, from an image of the sample treated with the dye, said computer-readable medium encoded with a computer program comprising:

an executable portion configured for determining a transmittance of the sample treated with the dye from a color image of the treated sample, the image comprising a plurality of pixels, in each of a red, green, and blue channel of an RGB color space and for each pixel of the image so as to form an RGB triplet for each pixel;

an executable portion configured for grouping the RGB triplets according to the minimum transmittance in the red, green, and blue channels for the respective RGB triplet;

an executable portion configured for normalizing each group of RGB triplets by summing the transmittances in each of the respective red, green, and blue channels and then dividing each of the summed transmittances by the number of RGB triplets in the respective group so as to form respective normalized RGB triplets; and an executable portion configured for tabulating the normalized RGB triplets according to the minimum transmittance of each normalized RGB triplet so as to form a correspondence table for the dye, the correspondence table extending in transmittance increments between 0% and 100% transmittance.

58. A computer-readable medium encoded with a computer program according to claim 57 further comprising an executable portion configured for directing a color image acquisition device to capture a magnified digital image of a sample treated with the dye, the image acquisition device comprising at least one of an RGB-configured scanner and a microscope operably engaged with an RGB camera.

59. A computer-readable medium encoded with a computer program according to claim 57 further comprising an executable portion configured for determining, when a transmittance increment in the correspondence table is without a normalized RGB triplet, an approximated transmittance in each of the red, green, and blue channels so as to form an approximated normalized RGB triplet for that transmittance increment.

60. A computer-readable medium encoded with a computer program according to claim 59 wherein the executable portion for determining the approximated normalized RGB triplet is further configured for determining a reference transmittance increment having a normalized RGB triplet, both at a higher transmittance increment and a lower transmittance increment in the correspondence table, with respect to the transmittance increment without the normalized RGB triplet, and then interpolating between the respective transmittances in each of the red, green, and blue channels of the reference transmittance increments so as to form an approximated normalized RGB triplet for the transmittance increment without the normalized RGB triplet.

61. A computer-readable medium encoded with a computer program according to claim 57 wherein the executable portion for grouping the RGB triplets is further configured for applying a significance threshold for the number of RGB triplets in a group and, for any group failing to meet the significance threshold, discarding the RGB triplets therein as being insignificant.

62. A computer-readable medium encoded with a computer program according to claim 57 further comprising an executable portion configured for plotting the RGB triplets for the pixels of the image in an RGB color space so as to provide a three-dimensional RGB representation of the respective dye.

63. A computer-readable medium encoded with a computer program according to claim 57 further comprising an executable portion configured for plotting the normalized RGB triplets in an RGB color space so as to obtain a characteristic RGB path of the respective dye through the RGB color space.

64. A computer-readable medium encoded with a computer program according to claim 57 further comprising an executable portion configured for plotting the normalized RGB triplets on a one-dimensional scale so as to graphically represent the correspondence table.

65. A computer-readable medium encoded with a computer program according to claim 58 further comprising an executable portion configured for directing the image acquisition device and the computer device to cooperate to form a chromatic aberration-corrected video-microscopy system.

66. A computer-readable medium encoded with a computer program according to claim 57 wherein the executable portion for determining a transmittance of the treated sample is further configured for directing a measurement of a transmitted intensity of light transmitted through the sample in each of the red, green, and blue channels.

67. A computer-readable medium encoded with a computer program according to claim 57 further comprising an executable portion configured for directing a light source to illuminate the sample under Koehler illumination conditions.

68. A computer-readable medium encoded with a computer program configured for modeling plurality of dyes from a corresponding plurality of samples using an image of each sample, each sample being treated with a different one of the plurality of dyes, said computer-readable medium encoded with a computer program comprising:

an executable portion configured for forming a correspondence table for each of the plurality or dyes from a magnified digital image of the respective sample captured by an image acquisition device, the image acquisition device comprising at least one of an RGB-configured scanner and a microscope operably engaged with an RGB camera comprising; determining a transmittance of a sample treated with the respective dye from a color image of the treated sample, the image comprising a plurality of pixels, in each of a red, green, and blue channel of an RGB color space of and for each pixel of the image so as to form an RGB triplet for each pixel; grouping the RGB triplets according to the minimum transmittance in the red, green, and blue channels for the respective RGB triplet; normalizing each group of RGB triplets by summing the transmittances in each of the respective red, green, and blue channels and then dividing each of the summed transmittances by the number of RGB triplets in the respective group so as to form respective normalized RGB triplets; and tabulating the normalized RGB triplets according to the minimum transmittance of each normalized RGB triplet so as to form the correspondence table for the respective dye, the correspondence table extending in transmittance increments between 0% and 100% transmittance; and an executable portion configured for orthogonally adding the correspondence tables of the plurality of dyes so as to form a dye space representation of the plurality of dyes, the dye space representation having one dimension for each dye and providing a reference model for a combination of the plurality of dyes.

69. A computer-readable medium encoded with a computer program according to claim 68 further comprising an executable portion configured for directing a color image acquisition device to capturing a magnified digital image of each respective sample, the image acquisition device comprising at least one of an RGB-configured scanner and a microscope operably engaged with an RGB camera.

70. A computer-readable medium encoded with a computer program according to claim 68 further comprising an executable portion configured for determining, when a transmittance increment in the correspondence table is without a normalized RGB triplet, an approximated transmittance in each of the red, green, and blue channels so as to form an approximated normalized RGB triplet for that transmittance increment.

71. A computer-readable medium encoded with a computer program according to claim 70 wherein the executable portion for determining the approximated normalized RGB triplet is further configured for determining a reference transmittance increment having a normalized RGB triplet, both at a higher transmittance increment and a lower transmittance increment in the correspondence table, with respect to the transmittance increment without the normalized RGB triplet, and then interpolating between the respective transmittances in each of the red, green, and blue channels of the reference transmittance increments so as to form an approximated normalized RGB triplet for the transmittance increment without the normalized RGB triplet.

72. A computer-readable medium encoded with a computer program according to claim 68 wherein the executable portion for forming a correspondence table for each of the plurality of dyes is further configured for applying a significance threshold for the number of RGB triplets in a group and, for any group failing to meet the significance threshold, to discard the RGB triplets therein as being insignificant.

73. A computer-readable medium encoded with a computer program according to claim 68 further comprising an executable portion configured for plotting the RGB triplets for the pixels of the image in an RGB color space so as to provide a three-dimensional RGB representation of the respective dye.

74. A computer-readable medium encoded with a computer program according to claim 68 further comprising an executable portion configured for plotting the RGB triplets for the pixels of the images for each of the plurality of dyes in an RGB color space so as to obtain a three-dimensional representation of a combination of the plurality of dyes.

75. A computer-readable medium encoded with a computer program according to claim 68 further comprising an executable portion configured for plotting the normalized RGB triplets in an RGB color space so as to obtain a characteristic RGB path of the respective dye through the RGB color space.

76. A computer-readable medium encoded with a computer program according to claim 68 further comprising an executable portion configured for plotting the normalized RGB triplets on a one-dimensional scale so as to graphically represent the correspondence table.

77. A computer-readable medium encoded with a computer program according to claim 68 wherein the executable portion for orthogonally adding the correspondence tables of the plurality of dyes is further configured for orthogonally adding the correspondence tables of the plurality of dyes according to the Lambert-Beer law.

78. A computer-readable medium encoded with a computer program according to claim 68 further comprising an executable portion configured for plotting the dye space representation or the plurality of dyes on a scale having a number of dimensions corresponding to the number of dyes.

79. A computer-readable medium encoded with a computer program according to claim 68 wherein the executable portion for orthogonally adding the correspondence tables of the plurality of dyes is further configured for orthogonally adding the correspondence tables of the plurality of dyes so as to form a resultant correspondence table for the combined plurality of dyes the resultant correspondence table comprising a plurality of resultant RGB triplets extending between 0% and 100% transmittance.

80. A computer-readable medium encoded with a computer program according to claim 69 further comprising an executable portion configured to direct the image acquisition device and the computer device to cooperate to form a chromatic aberration-corrected video-microscopy system.

81. A computer-readable medium encoded with a computer program according to claim 68 wherein the executable portion for forming a correspondence table for each of the plurality of dyes is further configured for directing a measurement of a transmitted intensity of light transmitted through the sample in each of the red, green, and blue channels.

82. A computer-readable encoded a computer program according to claim 68 further comprising an executable portion configured for directing a light source to illuminate the sample under Koehler illumination conditions.

* * * * *

UNITED STATES PATENT AND TRADEMARK OFFICE
CERTIFICATE OF CORRECTION

PATENT NO. : 7,133,547 B2  Page 1 of 1
APPLICATION NO. : 10/057729
DATED : November 7, 2006
INVENTOR(S) : Marcelpoil et al.

It is certified that error appears in the above-identified patent and that said Letters Patent is hereby corrected as shown below:

Column 25,
Line 63: "am" should read --an--

Column 26,
Line 1: "group RGB" should read --group of RGB--

Column 27,
Line 2: "dyes,said" should read --dyes, said--

Column 30,
Line 13: "ms" should read --as--

Column 34,
Line 57: "or" should read --of--

Signed and Sealed this

Twenty-second Day of May, 2007

JON W. DUDAS
*Director of the United States Patent and Trademark Office*